(12) United States Patent
Chen

(10) Patent No.: US 11,479,555 B2
(45) Date of Patent: Oct. 25, 2022

(54) SUBSTITUTED 1,2-DIHYDRO-3H-PYRAZOLO [3,4-D]PYRIMIDIN-3-ONES AS INHIBITORS OF WEE-1 KINASE

(71) Applicant: Newave Pharmaceutical Inc., Pleasanton, CA (US)

(72) Inventor: Yi Chen, Pleasanton, CA (US)

(73) Assignee: Newave Pharmaceutical Inc., Pleasanton, CA (US)

(*) Notice: Subject to any disclaimer, the term of this patent is extended or adjusted under 35 U.S.C. 154(b) by 5 days.

(21) Appl. No.: 16/959,449

(22) PCT Filed: Feb. 22, 2019

(86) PCT No.: PCT/US2019/019146
§ 371 (c)(1),
(2) Date: Jul. 1, 2020

(87) PCT Pub. No.: WO2019/165204
PCT Pub. Date: Aug. 29, 2019

(65) Prior Publication Data
US 2021/0061807 A1    Mar. 4, 2021

Related U.S. Application Data

(60) Provisional application No. 62/787,661, filed on Jan. 2, 2019, provisional application No. 62/634,519, filed on Feb. 23, 2018.

(51) Int. Cl.
| | | |
|---|---|---|
| *A61K 31/519* | (2006.01) | |
| *C07D 487/04* | (2006.01) | |
| *A61P 35/00* | (2006.01) | |

(52) U.S. Cl.
CPC .......... *C07D 487/04* (2013.01); *A61P 35/00* (2018.01)

(58) Field of Classification Search
CPC .................. A61K 31/519; C07D 487/04
USPC ........................ 514/262.1; 544/256
See application file for complete search history.

(56) References Cited

U.S. PATENT DOCUMENTS 7,834,019 B2 * 11/2010 Sagara ............... A61K 31/4162
514/252.16

FOREIGN PATENT DOCUMENTS

| EP | 2017278 A1 | 1/2009 |
|---|---|---|
| WO | 2017/075629 A2 | 5/2017 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
International Search Report and Written Opinion for Application No. PCT/US2019/019146, dated Jun. 24, 2019, 16 pages.

* cited by examiner

*Primary Examiner* — Douglas M Willis
(74) *Attorney, Agent, or Firm* — McCarter & English, LLP; Yu Lu; Zhongyu "Alex" Wang

(57) ABSTRACT

The disclosure includes compounds of Formula (I)

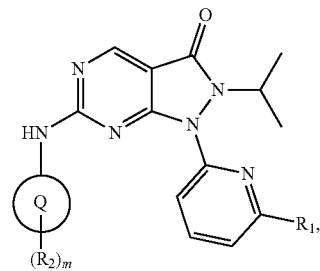

wherein Q, $R_1$, $R_2$, and m are defined herein. Also disclosed is a method for treating a neoplastic disease with these compounds.

9 Claims, No Drawings

SUBSTITUTED 1,2-DIHYDRO-3H-PYRAZOLO[3,4-D] PYRIMIDIN-3-ONES AS INHIBITORS OF WEE-1 KINASE

CROSS-REFERENCES TO RELATED APPLICATIONS

This application is a U.S. national stage application, filed under 35 U.S.C. § 371(c), of International Application No. PCT/US2019/019146, filed on Feb. 22, 2019, which claims the benefit of the filing date under 35 U.S.C. 119(e) to U.S. Provisional Patent Application No. 62/634,519, filed on Feb. 23, 2018, and U.S. Provisional Patent Application No. 62/787,661, filed on Jan. 2, 2019. The entire contents of each of the aforementioned applications are incorporated herein by reference.

BACKGROUND

Cells have a checkpoint mechanism of such that, when the DNA therein is damaged, then the cells temporarily stop the cell cycle and repair the damaged DNA (*Cell Proliferation*, Vol. 33, pp. 261-274). In about a half of human cancers, a cancer-suppressor gene, p53 is mutated or depleted and the cells thereby have lost the G1 checkpoint function thereof. However, such cancer cells still keep the G2 checkpoint function remaining therein, which is considered to be one factor of lowering the sensitivity of the cells to DNA-active anticancer agents and to radiations.

A Wee1 kinase is a tyrosine kinase that participates in the G2 checkpoint of a cell cycle. Wee1 phosphorylates Cdc2 (Cdk1) tyrosine 15 that participates in the progress to the M stage from the G2 stage in a cell cycle, thereby inactivating Cdc2 and temporarily stopping the cell cycle at the G2 stage (*The EMBO Journal*, Vol. 12, pp. 75-85). Accordingly, in cancer cells having lost the p53 function therein, it is considered that the G2 checkpoint function by Wee1 is important for repairing the damaged DNA so as to evade the cell death. Heretofore, it has been reported that the Wee1 expression reduction by RNA interference or the Wee1 inhibition by compounds may increase the sensitivity of cancer cells to adriamycin, X ray and gamma ray (*Cancer Biology & Therapy*, Vol. 3, pp. 305-313; *Cancer Research*, Vol. 61, pp. 8211-8217). From the above, it is considered that a Wee1 inhibitor may inhibit the G2 checkpoint function of p53-depleted cancer cells, thereby enhancing the sensitivity of the cells to DNA-active anticancer agents and to radiations.

As a low-molecular Wee1 kinase inhibitor, for example, known compounds are described in US Application 2005/0250836, WO2003/091255, WO2009/054332, WO2008133866, U.S. Pat. No. 7,834,019. AZD1775 is a highly selective, potent, ATP competitive, small molecule inhibitor of WEE1 kinase with an enzyme IC$_{50}$ of 5.18 nM. In vitro, AZD1775 inhibits WEE1 activity and induces DNA damage as well as G2 checkpoint escape in cell based assays with an EC50 of ~80 nM. AZD1775 increases cytotoxicity when used in combination with DNA damaging agents, such as gemcitabine, cisplatin, carboplatin and topotecan, in p53-deficient cell lines. In vivo, AZD1775 is well tolerated and shows enhancement of anti-tumor efficacy by gemcitabine, carboplatin, cisplatin, 5-fluorouracil (5-FU) and capecitabine in nude rat xenograft tumor models. Similarly, in nude mouse xenograft models, AZD1775 treatment results in significant tumor growth inhibition at tolerated doses, and also enhances the anti-tumor growth effect of gemcitabine, carboplatin, and radiation therapy. Unfortunately, AZD-1775 has poor CNS penetration in mice and the normal brain to whole blood ratio following a single AZD-1775 dose was 5%, which may limit its applications of in brain tumors. [Clin Cancer Res. 2015 Apr. 15; 21(8):1916-24].

Although the Wee1 inhibitors such as AZD1775 have made a significant contribution to the art, there is a continuing search in this field of art for improved pharmaceuticals, in particular with good CNS penetration.

SUMMARY OF THE INVENTION

This invention provides compounds of the Formula (I) or an N-oxide thereof, or a pharmaceutically acceptable salt, solvate, polymorph or tautomer of said compound of formula (I-0) or N-oxide thereof:

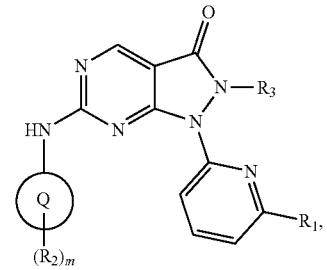

wherein
Q is a aryl or heteroaryl;
R$_1$ is H, D,

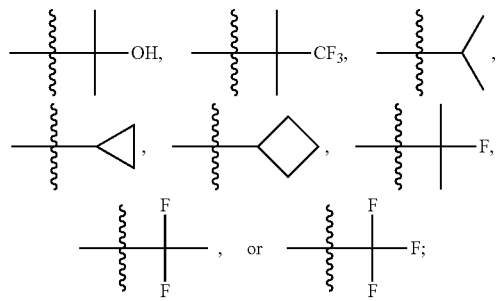

each of R$_2$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, cyano, OR$_a$, SR$_a$, alkyl-R$_a$, NH(CH$_2$)$_p$R$_a$, C(O)R$_a$, S(O)R$_a$, SO$_2$R$_a$, C(O)OR$_a$, OC(O)R$_a$, NR$_b$R$_c$, C(O)N(R$_b$)R$_c$, N(R$_b$)C(O)R$_c$, —P(O)R$_b$R$_c$, -alkyl-P(O)R$_b$R$_c$, —S(O)(=N(R$_b$))R$_c$, —N=S(O)R$_b$R$_c$, =NR$_b$, SO$_2$N(R$_b$)R$_c$, or N(R$_b$)SO$_2$R$_c$, in which said cycloalkyl, cycloalkenyl, heterocycloalkyl, heterocycloalkenyl, aryl, heteroaryl is optionally substituted with one or more R$_d$;

R$_3$ is alkyl, or alkenyl (alternatively, R$_3$ is C$_{1-4}$alkyl optionally substituted with D or halo; C$_{2-4}$alkenyl; or C$_{3-4}$cycloalkyl);

R$_a$, R$_b$, R$_c$ and R$_d$, independently, is H, D, alkyl, spiroalkyl, alkenyl, alkynyl, halo, cyano, amine, nitro, hydroxy, =O, —P(O)R$_b$R$_c$, -alkyl-P(O)R$_b$R$_c$, —S(O)(=N(R$_b$))R$_c$, —N=S(O)R$_b$R$_c$, =NR$_b$, C(O)NHOH, C(O)OH, C(O)NH$_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

two of $R_2$ group, taken together with the atom to which they are attached, may optionally form a cycloalkyl or heterocycloalkyl optionally substituted with one or more $R_d$; and m is 0, 1, 2, 3, or 4.

In one embodiment, the compound is represented by Formula (I):

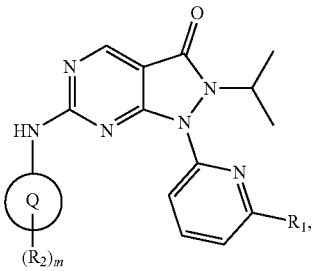

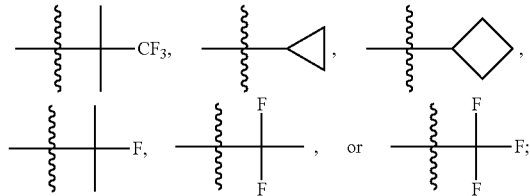

wherein
Q is a aryl or heteroaryl;
$R_1$ is H, D, —CH(CH$_3$)$_2$, —C(CF$_3$)(CD$_3$)$_2$, each of $R_2$, independently, is H, D, alkyl, spiroalkyl, alkenyl, alkynyl, cycloalkyl, cycloalkenyl, heterocycloalkyl, spiroheterocycloalkyl, heterocycloalkenyl, aryl, heteroaryl, halo, nitro, cyano, OR$_a$, SR$_a$, alkyl-R$_a$, NH(CH$_2$)$_p$R$_a$, C(O)R$_a$, S(O)R$_a$, SO$_2$R$_a$, C(O)OR$_a$, OC(O)R$_a$, NR$_b$R$_c$, C(O)N(R$_b$)R$_c$, N(R$_b$)C(O)R$_c$, —P(O)R$_b$R$_c$, -alkyl-P(O)R$_b$R$_c$, —S(O)(=N(R$_b$))R$_c$, —N=S(O)R$_b$R$_c$, =NR$_b$, SO$_2$N(R$_b$)R$_c$, or N(R$_b$)SO$_2$R$_c$, in which said cycloalkyl, cycloalkenyl, heterocycloalkyl, heterocycloalkenyl, aryl, heteroaryl is optionally substituted with one or more $R_d$;

$R_a$, $R_b$, $R_c$ and $R_d$, independently, is H, D, alkyl, spiroalkyl, alkenyl, alkynyl, halo, cyano, amine, nitro, hydroxy, =O, —P(O)R$_b$R$_c$, -alkyl-P(O)R$_b$R$_c$, —S(O)(=N(R$_b$))R$_c$, —N=S(O)R$_b$R$_c$, =NR$_b$, C(O)NHOH, C(O)OH, C(O)NH$_2$, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl, in which said alkyl, cycloalkyl, cycloalkenyl, heterocycloalkyl, heterocycloalkenyl, aryl, heteroaryl is optionally substituted with one or more $R_e$;

$R_e$ is H, D, alkyl, spiroalkyl, alkenyl, alkynyl, halo, cyano, amine, nitro, hydroxy, =O, C(O)NHOH, alkoxy, alkoxyalkyl, haloalkyl, hydroxyalkyl, aminoalkyl, alkylcarbonyl, alkoxycarbonyl, alkylcarbonylamino, alkylamino, oxo, halo-alkylamino, cycloalkyl, cycloalkenyl, heterocycloalkyl, spiroheterocycloalkyl, heterocycloalkenyl, aryl, or heteroaryl;

two of $R_2$ group, taken together with the atom to which they are attached, may optionally form a cycloalkyl or heterocycloalkyl optionally substituted with one or more $R_d$; and m is 0, 1, 2, 3, or 4.

In one embodiment, the compound is represented by Formula (II):

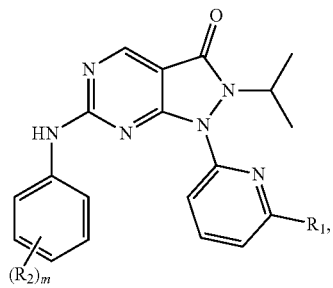

and the remaining variables are as defined herein for Formula (I-0) or Formula (I).

In one embodiment, the compound is represented by Formula (III):

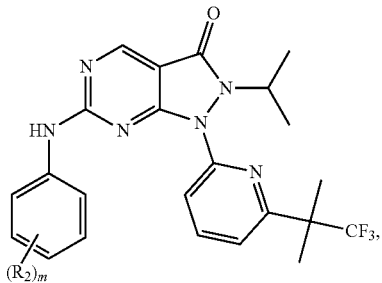

and the remaining variables are as defined herein for Formula (I-0), Formula (I), or Formula (II).

In one embodiment, the compound is represented by Formula (I-0), Formula (I), Formula (II), or Formula (III), $R_2$, independently, is H, D, halo, nitro, cyano, $C_{1-4}$alkyl, $C_{1-4}$haloalkyl, $C_{1-4}$alkoxy, 4-7 numbered monocyclic heterocycloalkyl, 4-7 numbered monocyclic heterocycloalkenyl, 5-6 membered heteroaryl wherein the 4-7 numbered monocyclic heterocycloalkyl, 4-7 numbered monocyclic heterocycloalkenyl, or 5-6 membered heteroaryl is optionally substituted with halo, OH, nitro, cyano, $C_{1-4}$alkyl, $C_{1-4}$haloalkyl, $C_{1-4}$alkoxy, C(O)OH, C(O)C$_{1-4}$alkyl, C(O)OC$_{1-4}$alkyl, C(O)NH$_2$, NH$_2$, or $C_{3-6}$cycloalkyl; and m is 0, 1, or 2; the remaining variables are as defined herein for Formula (I-0), Formula (I), Formula (II), or Formula (III).

In a preferred embodiment, each of $R_2$, independently, is H; F; $C_{1-4}$alkyl; pyrrolidinyl optionally substituted with N(CH$_3$)$_2$; morpholinyl; piperazinyl optionally substituted with $C_{1-4}$alkyl, $C_{1-4}$haloalkyl, or $C_{3-6}$cycloalkyl; and m is 0 or 1.

In a preferred embodiment, $R_1$ is H, —CH(CH$_3$)$_2$, —C(CF$_3$)(CD$_3$)$_2$,

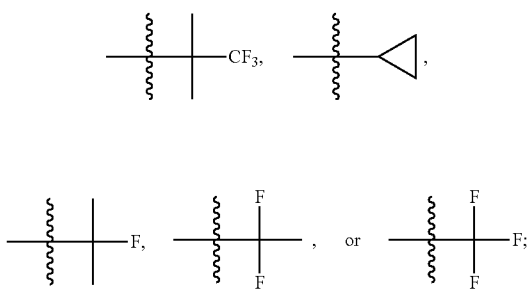

Compounds of the invention may contain one or more asymmetric carbon atoms. Accordingly, the compounds may exist as diastereomers, enantiomers, or mixtures thereof. Each of the asymmetric carbon atoms may be in the R or S configuration, and both of these configurations are within the scope of the invention.

A modified compound of any one of such compounds including a modification having an improved (e.g., enhanced, greater) pharmaceutical solubility, stability, bioavailability, and/or therapeutic index as compared to the unmodified compound is also contemplated. Exemplary modifications include (but are not limited to) applicable prodrug derivatives, and deuterium-enriched compounds.

It should be recognized that the compounds of the present invention may be present and optionally administered in the form of salts or solvates. The invention encompasses any pharmaceutically acceptable salts and solvates of any one of the above-described compounds and modifications thereof.

Also within the scope of this invention is a pharmaceutical composition containing one or more of the compounds, modifications, and/or salts and thereof described above for use in treating a neoplastic disease, therapeutic uses thereof, and use of the compounds for the manufacture of a medicament for treating the disease/disorder.

This invention also relates to a method of treating a neoplastic disease, including but not limited to lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease, by administering to a subject in need thereof an effective amount of one or more of the compounds, modifications, and/or salts, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

DETAILED DESCRIPTION OF THE INVENTION

Exemplary compounds described herein include, but are not limited to, the following:

2-allyl-1-(6-(2-hydroxypropan-2-yl)pyridin-2-yl)-6-((1-(1-methylpiperidin-4-yl)-1H-pyrazol-4-yl)amino)-1,2-dihydro-3H-pyrazolo[3,4-d]pyrimidin-3-one, 2-allyl-6-((1-((1r,4r)-4-(4-(cyclopropylmethyl)piperazin-1-yl)cyclohexyl)-1H-pyrazol-4-yl)amino)-1-(6-(2-hydroxypropan-2-yl)pyridin-2-yl)-1,2-dihydro-3H-pyrazolo[3,4-d]pyrimidin-3-one, 2-allyl-1-(6-(2-hydroxypropan-2-yl)pyridin-2-yl)-6-((1-((1r,4r)-4-morpholinocyclohexyl)-1H-pyrazol-4-yl)amino)-1,2-dihydro-3H-pyrazolo[3,4-d]pyrimidin-3-one, 2-allyl-1-(6-(2-hydroxypropan-2-yl)pyridin-2-yl)-6-((1-(1-(oxetan-3-yl)piperidin-4-yl)-1H-pyrazol-4-yl)amino)-1,2-dihydro-3H-pyrazolo[3,4-d]pyrimidin-3-one, 2-allyl-6-((1-(1-(3,3-difluorocyclopentyl)piperidin-4-yl)-1H-pyrazol-4-yl)amino)-1-(6-(2-hydroxypropan-2-yl)pyridin-2-yl)-1,2-dihydro-3H-pyrazolo[3,4-d]pyrimidin-3-one, 2-allyl-1-(6-(2-hydroxypropan-2-yl)pyridin-2-yl)-6-((1-(1-isopropylpiperidin-4-yl)-1H-pyrazol-4-yl)amino)-1,2-dihydro-3H-pyrazolo[3,4-d]pyrimidin-3-one, 2-allyl-1-(6-(2-hydroxypropan-2-yl)pyridin-2-yl)-6-((1-(1'-isopropyl-[1,4'-bipiperidin]-4-yl)-1H-pyrazol-4-yl)amino)-1,2-dihydro-3H-pyrazolo[3,4-d]pyrimidin-3-one, 2-allyl-6-((1-(1-(4,4-difluorocyclohexyl)piperidin-4-yl)-1H-pyrazol-4-yl)amino)-1-(6-(2-hydroxypropan-2-yl)pyridin-2-yl)-1,2-dihydro-3H-pyrazolo[3,4-d]pyrimidin-3-one, 2-allyl-1-(6-(2-hydroxypropan-2-yl)pyridin-2-yl)-6-((1-isopropyl-1H-pyrazol-4-yl)amino)-1,2-dihydro-3H-pyrazolo[3,4-d]pyrimidin-3-one, 2-allyl-6-((1-cyclopentyl-1H-pyrazol-4-yl)amino)-1-(6-(2-hydroxypropan-2-yl)pyridin-2-yl)-1,2-dihydro-3H-pyrazolo[3,4-d]pyrimidin-3-one, 2-allyl-6-((1-cyclohexyl-1H-pyrazol-4-yl)amino)-1-(6-(2-hydroxypropan-2-yl)pyridin-2-yl)-1,2-dihydro-3H-pyrazolo[3,4-d]pyrimidin-3-one, 2-isopropyl-6-((1-(1-methylpiperidin-4-yl)-1H-pyrazol-4-yl)amino)-1-(6-(1,1,1-trifluoro-2-methylpropan-2-yl)pyridin-2-yl)-1,2-dihydro-3H-pyrazolo[3,4-d]pyrimidin-3-one, 6-((1-((1r,4r)-4-(4-(cyclopropylmethyl)piperazin-1-yl)cyclohexyl)-1H-pyrazol-4-yl)amino)-1-(6-(2-fluoropropan-2-yl)pyridin-2-yl)-2-isopropyl-1,2-dihydro-3H-pyrazolo[3,4-d]pyrimidin-3-one, 6-((1-cyclohexyl-1H-pyrazol-4-yl)amino)-1-(6-(1,1-difluoroethyl)pyridin-2-yl)-2-isopropyl-1,2-dihydro-3H-pyrazolo[3,4-d]pyrimidin-3-one, 1-(6-cyclopropylpyridin-2-yl)-6-((1-(1-(4,4-difluorocyclohexyl)piperidin-4-yl)-1H-pyrazol-4-yl)amino)-2-isopropyl-1,2-dihydro-3H-pyrazolo[3,4-d]pyrimidin-3-one, 2-isopropyl-6-((1-(1'-isopropyl-[1,4'-bipiperidin]-4-yl)-1H-pyrazol-4-yl)amino)-1-(6-(trifluoromethyl)pyridin-2-yl)-1,2-dihydro-3H-pyrazolo[3,4-d]pyrimidin-3-one, 2-isopropyl-6-((4-(4-methylpiperazin-1-yl)phenyl)amino)-1-(pyridin-2-yl)-1,2-dihydro-3H-pyrazolo[3,4-d]pyrimidin-3-one, 2-isopropyl-1-(6-isopropylpyridin-2-yl)-6-((4-(4-methylpiperazin-1-yl)phenyl)amino)-1,2-dihydro-3H-pyrazolo[3,4-d]pyrimidin-3-one, 1-(6-(2-hydroxypropan-2-yl)pyridin-2-yl)-2-isopropyl-6-((4-(4-methylpiperazin-1-yl)phenyl)amino)-1,2-dihydro-3H-pyrazolo[3,4-d]pyrimidin-3-one, 2-isopropyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one,
6-((3-fluoro-4-(4-methylpiperazin-1-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one.
1-(6-(2-fluoropropan-2-yl)pyridin-2-yl)-2-isopropyl-6-((4-(4-methylpiperazin-1-yl)phenyl)amino)-1,2-dihydro-3H-pyrazolo[3,4-d]pyrimidin-3-one,
1-(6-(1,1-difluoroethyl)pyridin-2-yl)-2-isopropyl-6-((4-(4-methylpiperazin-1-yl)phenyl)amino)-1,2-dihydro-3H-pyrazolo[3,4-d]pyrimidin-3-one,
1-(6-cyclopropylpyridin-2-yl)-2-isopropyl-6-((4-(4-methylpiperazin-1-yl)phenyl)amino)-1,2-dihydro-3H-pyrazolo[3,4-d]pyrimidin-3-one,
2-cyclopropyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one,
2-cyclopropyl-1-(6-(2-fluoropropan-2-yl)pyridin-2-yl)-6-((4-(4-methylpiperazin-1-yl)phenyl)amino)-1,2-dihydro-3H-pyrazolo[3,4-d]pyrimidin-3-one,
2-cyclopropyl-1-(6-(1,1-difluoroethyl)pyridin-2-yl)-6-((4-(4-methylpiperazin-1-yl)phenyl)amino)-1,2-dihydro-3H-pyrazolo[3,4-d]pyrimidin-3-one,
2-cyclopropyl-1-(6-cyclopropylpyridin-2-yl)-6-((4-(4-methylpiperazin-1-yl)phenyl)amino)-1,2-dihydro-3H-pyrazolo[3,4-d]pyrimidin-3-one,
2-isopropyl-6-((4-(4-methylpiperazin-1-yl)phenyl)amino)-1-(6-(trifluoromethyl)pyridin-2-yl)-1,2-dihydro-3H-pyrazolo[3,4-d]pyrimidin-3-one,
(R)-6-((4-(3-(dimethylamino)pyrrolidin-1-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one,
(S)-6-((4-(3-(dimethylamino)pyrrolidin-1-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one,
6-((4-fluorophenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one,
1-(6-cyclopropylpyridin-2-yl)-2-isopropyl-6-((4-(4-(2,2,2-trifluoroethyl)piperazin-1-yl)phenyl)amino)-1,2-dihydro-3H-pyrazolo[3,4-d]pyrimidin-3-one,
6-((4-(4-cyclopropylpiperazin-1-yl)phenyl)amino)-1-(6-cyclopropylpyridin-2-yl)-2-isopropyl-1,2-dihydro-3H-pyrazolo[3,4-d]pyrimidin-3-one,
1-(6-cyclopropylpyridin-2-yl)-6-((4-(4-ethylpiperazin-1-yl)phenyl)amino)-2-isopropyl-1,2-dihydro-3H-pyrazolo[3,4-d]pyrimidin-3-one,
1-(6-cyclopropylpyridin-2-yl)-2-isopropyl-6-((4-(piperidin-3-yl)phenyl)amino)-1,2-dihydro-3H-pyrazolo[3,4-d]pyrimidin-3-one,
2-cyclobutyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one,
1-(6-(1,1-difluoroethyl)pyridin-2-yl)-2-isopropyl-6-((5-(4-methylpiperazin-1-yl)pyridin-2-yl)amino)-1,2-dihydro-3H-pyrazolo[4,3-c]pyridin-3-one,
2-isopropyl-6-((2-(oxetan-3-yl)-1,2,3,4-tetrahydroisoquinolin-6-yl)amino)-1-(6-(1,1,1-trifluoro-2-methylpropan-2-yl)pyridin-2-yl)-1,2-dihydro-3H-pyrazolo[3,4-d]pyrimidin-3-one,
2-isopropyl-6-((3-methyl-4-morpholinophenyl)amino)-1-(6-(1,1,1-trifluoro-2-methylpropan-2-yl)pyridin-2-yl)-1,2-dihydro-3H-pyrazolo[3,4-d]pyrimidin-3-one,
6-((4-(8-oxa-3-azabicyclo [3.2.1]octan-3-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one,
6-((4-(4-methylpiperazin-1-yl)phenyl)amino)-2-(propan-2-yl-1,1,1,3,3,3-d6)-1-(6-(1,1,1-trifluoro-2-methylpropan-2-yl)pyridin-2-yl)-1,2-dihydro-3H-pyrazolo[3,4-d]pyrimidin-3-one,
6-((4-(4-methylpiperazin-1-yl)phenyl)amino)-2-(propan-2-yl-1,1,1,3,3,3-d6)-1-(6-(1,1,1-trifluoro-2-(methyl-d3)propan-2-yl-3,3,3-d3)pyridin-2-yl)-1,2-dihydro-3H-pyrazolo [3,4-d]pyrimidin-3-one.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, and the deuterium-enriched compounds. For example:

Prodrug derivatives: prodrugs, upon administration to a subject, will converted in vivo into active compounds of the present invention [*Nature Reviews of Drug Discovery*, 2008, Volume 7, p255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2$H) is a stable, non-radioactive isotope of hydrogen and has an atomic weight of 2.0144. Hydrogen naturally occurs as a mixture of the isotopes $^X$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

It should be recognized that the compounds of the present invention may be present and optionally administered in the form of salts, and solvates. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptonate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate, methyl cellulose, hydroxyethyl cellulose, carboxymethylcellulose sodium), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used.

As used herein, "acyl" means a carbonyl containing substituent represented by the formula —C(O)—R in which R is H, alkyl, a carbocycle, a heterocycle, carbocycle-substituted alkyl or heterocycle-substituted alkyl wherein the alkyl, alkoxy, carbocycle and heterocycle are as defined herein. Acyl groups include alkanoyl (e.g. acetyl), aroyl (e.g. benzoyl), and heteroaroyl.

"Aliphatic" means a moiety characterized by a straight or branched chain arrangement of constituent carbon atoms and may be saturated or partially unsaturated with one or more double or triple bonds.

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "alkylamino" refers to an —N(R)-alkyl in which R can be H, alkyl, alkenyl, alkynyl, cycloalkyl, cycloalkenyl, heterocycloalkyl, heterocycloalkenyl, aryl, or heteroaryl.

"Alkoxy" means an oxygen moiety having a further alkyl substituent.

"Alkoxycarbonyl" means an alkoxy group attached to a carbonyl group.

"Oxoalkyl" means an alkyl, further substituted with a carbonyl group. The carbonyl group may be an aldehyde, ketone, ester, amide, acid or acid chloride.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl. The term "cycloalkenyl" refers to a non-aromatic hydrocarbon ring system having 3 to 30 carbons (e.g., $C_3$-$C_{12}$) and one or more double bonds. Examples include cyclopentenyl, cyclohexenyl, and cycloheptenyl.

The term "heterocycloalkyl" refers to a nonaromatic 5-8 membered monocyclic, 8-12 membered bicyclic, or 11-14 membered tricyclic ring system having one or more heteroatoms (such as O, N, S, P, or Se). Examples of heterocycloalkyl groups include, but are not limited to, piperazinyl, pyrrolidinyl, dioxanyl, morpholinyl, and tetrahydrofuranyl.

The term "heterocycloalkenyl" refers to a nonaromatic 5-8 membered monocyclic, 8-12 membered bicyclic, or 11-14 membered tricyclic ring system having one or more heteroatoms (such as O, N, S, P, or Se) and one or more double bonds.

The term "aryl" refers to a 6-carbon monocyclic, 10-carbon bicyclic, 14-carbon tricyclic aromatic ring system. Examples of aryl groups include, but are not limited to, phenyl, naphthyl, and anthracenyl. The term "heteroaryl" refers to an aromatic 5-8 membered monocyclic, 8-12 membered bicyclic, or 11-14 membered tricyclic ring system having one or more heteroatoms (such as O, N, S, P, or Se). Examples of heteroaryl groups include pyridyl, furyl, imidazolyl, benzimidazolyl, pyrimidinyl, thienyl, quinolinyl, indolyl, and thiazolyl.

Alkyl, alkenyl, alkynyl, cycloalkyl, heterocycloalkyl, cycloalkenyl, heterocycloalkenyl, alkylamino, aryl, and heteroaryl mentioned above include both substituted and unsubstituted moieties. Possible substituents on alkylamino, cycloalkyl, heterocycloalkyl, cycloalkenyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, arylamino, hydroxy, halo, oxo (O=), thioxo (S=), thio, silyl, $C_1$-$C_{10}$ alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl, carboxyl, and carboxylic ester. On the other hand, possible substituents on alkyl, alkenyl, or alkynyl include all of the above-recited substituents except $C_1$-$C_{10}$ alkyl, cycloalkyl, cycloalkenyl, heterocycloalkyl, heterocycloalkenyl, aryl, and heteroaryl can also be fused with each other.

"Amino" means a nitrogen moiety having two further substituents where each substituent has a hydrogen or carbon atom alpha bonded to the nitrogen. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Aromatic" means a moiety wherein the constituent atoms make up an unsaturated ring system, all atoms in the ring system are sp2 hybridized and the total number of pi electrons is equal to 4n+2. An aromatic ring may be such that the ring atoms are only carbon atoms or may include carbon and non-carbon atoms (see Heteroaryl).

"Carbamoyl" means the radical —OC(O)NR$_a$R$_b$ where R$_a$ and R$_b$ are each independently two further substituents where a hydrogen or carbon atom is alpha to the nitrogen. It is noted that carbamoyl moieties may include protected derivatives thereof. Examples of suitable protecting groups for carbamoyl moieties include acetyl, tert-butoxycarbonyl, benzyloxycarbonyl, and the like. It is noted that both the unprotected and protected derivatives fall within the scope of the invention.

"Carbonyl" means the radical —C(O)—. It is noted that the carbonyl radical may be further substituted with a variety of substituents to form different carbonyl groups including acids, acid halides, amides, esters, and ketones.

"Carboxy" means the radical —C(O)O—. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Formyl" means the radical —CH=O.

"Formimino" means the radical —HC=NH.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like.

"Hydroxy" means the radical —OH.

"Imine derivative" means a derivative comprising the moiety —C(=NR)—, wherein R comprises a hydrogen or carbon atom alpha to the nitrogen.

"Isomers" mean any compound having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture."

"Nitro" means the radical —NO$_2$.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

The term "substituted" means that an atom or group of atoms has replaced hydrogen as the substituent attached to another group. For aryl and heteroaryl groups, the term "substituted" refers to any level of substitution, namely mono-, di-, tri-, tetra-, or penta-substitution, where such substitution is permitted. The substituents are independently selected, and substitution may be at any chemically accessible position. The term "unsubstituted" means that a given moiety may consist of only hydrogen substituents through available valencies (unsubstituted).

If a functional group is described as being "optionally substituted," the function group may be either (1) not substituted, or (2) substituted. If a carbon of a functional group is described as being optionally substituted with one or more of a list of substituents, one or more of the hydrogen atoms on the carbon (to the extent there are any) may separately and/or together be replaced with an independently selected optional substituent.

"Sulfide" means —S—R wherein R is H, alkyl, carbocycle, heterocycle, carbocycloalkyl or heterocycloalkyl. Particular sulfide groups are mercapto, alkylsulfide, for example methylsulfide (—S-Me); arylsulfide, e.g., phenylsulfide; aralkylsulfide, e.g., benzylsulfide.

"Sulfinyl" means the radical —S(O)—. It is noted that the sulfinyl radical may be further substituted with a variety of substituents to form different sulfinyl groups including sulfinic acids, sulfinamides, sulfinyl esters, and sulfoxides.

"Sulfonyl" means the radical —S(O)(O)—. It is noted that the sulfonyl radical may be further substituted with a variety of substituents to form different sulfonyl groups including sulfonic acids, sulfonamides, sulfonate esters, and sulfones.

"Thiocarbonyl" means the radical —C(S)—. It is noted that the thiocarbonyl radical may be further substituted with a variety of substituents to form different thiocarbonyl groups including thioacids, thioamides, thioesters, and thioketones.

"Animal" includes humans, non-human mammals (e.g., non-human primates, rodents, mice, rats, hamsters, dogs, cats, rabbits, cattle, horses, sheep, goats, swine, deer, and the like) and non-mammals (e.g., birds, and the like).

"Bioavailability" as used herein is the fraction or percentage of an administered dose of a drug or pharmaceutical composition that reaches the systemic circulation intact. In general, when a medication is administered intravenously, its bioavailability is 100%. However, when a medication is administered via other routes (e.g., orally), its bioavailability decreases (e.g., due to incomplete absorption and first-pass metabolism). Methods to improve the bioavailability include prodrug approach, salt synthesis, particle size reduction, complexation, change in physical form, solid dispersions, spray drying, and hot-melt extrusion.

"Disease" specifically includes any unhealthy condition of an animal or part thereof and includes an unhealthy condition that may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means organic or inorganic salts of compounds of the present invention which are pharmaceutically acceptable, as defined above, and which possess the desired pharmacological activity. Such salts include acid addition salts formed with inorganic acids, or with organic acids. Pharmaceutically acceptable salts also include base addition salts which may be formed when acidic protons present are capable of reacting with inorganic or organic bases. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Pharmacophore," as defined by The International Union of Pure and Applied Chemistry, is an ensemble of steric and electronic features that is necessary to ensure the optimal supramolecular interactions with a specific biological target and to trigger (or block) its biological response. For example, Camptothecin is the pharmacophore of the well-known drug topotecan and irinotecan. Mechlorethamine is the pharmacophore of a list of widely used nitrogen mustard drugs like Melphalan, Cyclophosphamide, Bendamustine, and so on.

"Prodrug" means a compound that is convertible in vivo metabolically into an active pharmaceutical according to the present invention. For example, an inhibitor comprising a hydroxyl group may be administered as an ester that is converted by hydrolysis in vivo to the hydroxyl compound.

"Stability" in general refers to the length of time a drug retains its properties without loss of potency. Sometimes this is referred to as shelf life. Factors affecting drug stability include, among other things, the chemical structure of the drug, impurity in the formulation, pH, moisture content, as well as environmental factors such as temperature, oxidization, light, and relative humidity. Stability can be improved by providing suitable chemical and/or crystal modifications (e.g., surface modifications that can change hydration kinetics; different crystals that can have different properties), excipients (e.g., anything other than the active substance in the dosage form), packaging conditions, storage conditions, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrogen Mustards (e.g., Bendamustine, Cyclophosphamide, Melphalan, Chlorambucil, Isofosfamide), Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous antineoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F317I), ABL1(G250E), ABL1(H396P), ABL1 (M351T), ABL1(Q252H), ABL1(T315I), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-Kit(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDGFRa(D842V), PDGFRa(T674I), PDGFRa(V561D), RET (E762Q), RET(G691S), RET(M918T), RET(R749T), RET (R813Q), RET(V804L), RET(V804M), RET(Y79IF), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, gene therapy, RNAi cancer therapy, chemoprotective agents (e.g., amfostine, mesna, and dexrazoxane), antibody conjugate (e.g., brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, kinase inhibitors, epigenetic agents, HSP90 inhibitors, PARP inhibitors, and antibodies targeting VEGF, HER2, EGFR, CD50, CD20, CD30, CD33, etc.

In certain embodiments, the compounds of the invention are administered in combination with one or more of abarelix, abiraterone acetate, aldesleukin, alemtuzumab, altretamine, anastrozole, asparaginase, bendamustine, bevacizumab, bexarotene, bicalutamide, bleomycin, bortezombi, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

The invention further provides methods for the prevention or treatment of a neoplastic disease. In one embodiment, the invention relates to a method of treating a neoplastic disease, in a subject in need of treatment comprising administering to said subject a therapeutically effective amount of a compound of the invention. In one embodiment, the invention further provides for the use of a compound of the invention in the manufacture of a medicament for halting or decreasing a neoplastic disease.

In certain embodiments, the neoplastic disease is a lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome, or myeloproliferative disease.

It should be understood that the invention is not limited to the particular embodiments shown and described herein, but that various changes and modifications may be made without departing from the spirit and scope of the invention as defined by the claims.

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach to synthesize of Formula (I-0) compounds of

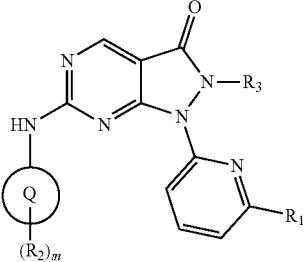

is described in Scheme 1. $R_1$, $R_2$, $R_3$, m, and Q in Scheme 1 are the same as those described in the Summary section above.

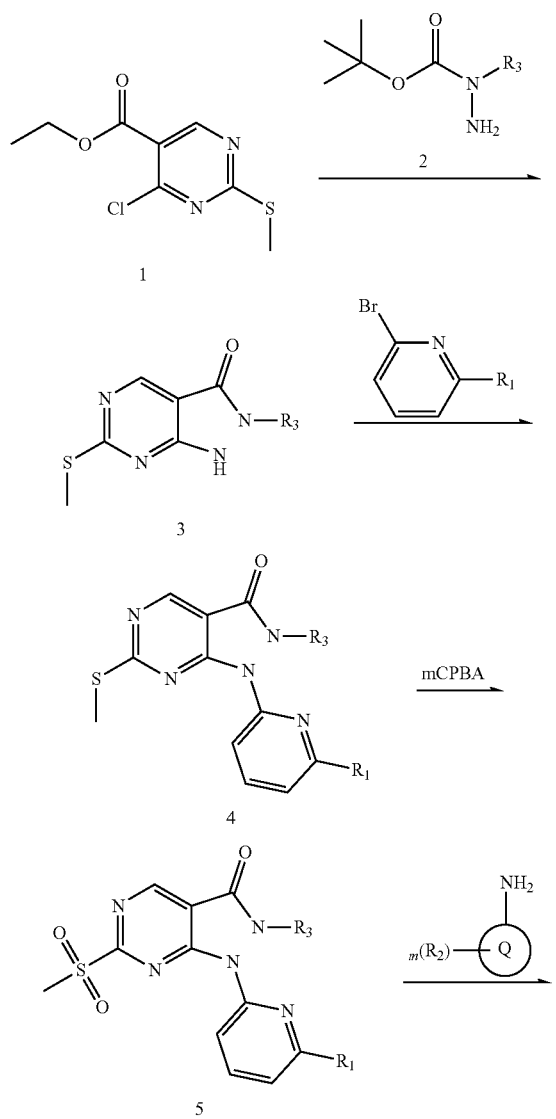

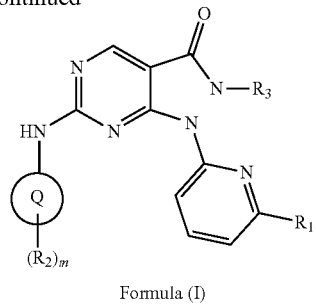

Formula (I)

In Scheme 1, the starting material ethyl 4-chloro-2-(methylthio)pyrimidine-5-carboxylate can react with appropriate hydrazine to form the intermediate 3, which can react with appropriate bromide to form the intermediate 4. After that, the intermediate 4 can be oxidized to form the intermediate 5, which can finally react with appropriate amine to yield the target compounds.

The similar strategy can be explored in the synthesis of Formulae (II) and Formulae (III) compounds by using different reagents and or staring materials.

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Where NMR data are presented, $^1$H spectra were obtained on XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Applied Biosystems API-100 mass spectrometer and Shimadzu SCL-10A LC column.

Example 1: Preparation of 2-allyl-1-(6-(2-hydroxypropan-2-yl)pyridin-2-yl)-6-((1-(1-methylpiperidin-4-yl)-1H-pyrazol-4-yl)amino)-1,2-dihydro-3H-pyrazolo[3,4-d]pyrimidin-3-one 250 g of tert-butyl hydrazinecarboxylate was added to toluene (3 L) solution of 280 g of phthalic anhydride. Using a Dean-Stark water separator, the reaction mixture was heated under reflux for 3 hours. This was cooled to room temperature, the formed solid was taken out through filtration to obtain 516 g of crude tert-butyl (1,3-dioxo-1,3-dihydro-2H-isoindol-2-yl)carbamate.

520 g of potassium carbonate, 43.3 g of benzyltriethylammonium chloride and 250 mL of allyl bromide were added in that order to acetonitrile (3.5 L) solution of the above compound, and stirred at room temperature for 18 hours. 1.5 L of water was added to the reaction solution, and the acetonitrile layer was separated and concentrated. One L of water was added to the residue and the aqueous layer, extracted with ethyl acetate, and the ethyl acetate layer was washed with saturated saline water, and then dried with anhydrous sodium sulfate. The solvent was evaporated away under reduced pressure, and the precipitated colorless solid was washed with hexane and dried to obtain 460 g of crude tert-butyl allyl(1,3-dioxo-1,3-dihydro-2H-isoindol-2-yl)carbamate.

With cooling in an ice bath, 100 mL of methylhydrazine was added to tetrahydrofuran (3.0 L) solution of the above compound, then restored to room temperature, and stirred for 18 hours. The precipitated insoluble matter was taken out through filtration, and the filtrate was concentrated. A mixed solvent of hexane/ethyl acetate (3/1) was added to the residue, and the precipitated insoluble matter was taken out through filtration. This operation was repeated five times, then the filtrate was concentrated under reduced pressure, the resulting residue was distilled under reduced pressure to obtain 211 g of the entitled compound as a pale yellow oily substance. ESI-MS Found: m/z[M+H]+ 173.4.

260 mL of N,N-diisopropylethylamine and 106 g of the hydrazine obtained in the above 1 were added to tetrahydrofuran (1.5 L) solution of 142 g of ethyl 4-chloro-2-(methylthio)pyridine-5-carboxylate, and stirred with heating under reflux for 18 hours. After cooled to room temperature, the reaction solution was evaporated under reduced pressure, and 500 mL of diethyl ether was added to the residue, and the precipitated solid was separated through filtration.

The filtrate was evaporated under reduced pressure, the residue was cooled in an ice bath, 400 mL of trifluoroacetic acid was gradually added thereto, and stirred at room temperature for 1 hour and then at 70° C. for 1 hour 2.4 mL of N,N'-dimethylethylenediamine was added to 1,4-dioxane (50 mL) solution of 4.44 g of 2-allyl-6-(methylthio)-1,2-dihydro-3H-pyrazolo[3,4-d]pyrimidin-3-one, 3.80 g of copper(I) iodide, 5.33 g of 2-iodopyridine and 3.80 g of potassium carbonate, and stirred overnight at 95° C. The reaction liquid was cooled, aqueous ammonia was added thereto and extracted with ethyl acetate, washed with saturated saline water and dried with anhydrous magnesium sulfate. The solvent was evaporated away under reduced pressure, and crystallized with ethyl acetate. 2-allyl-1-[6-(1-hydroxy-1-methylethyl)-2-pyridinyl]-6-(methylthio)-1,2-dihydro-3H-pyrazolo[3,4-d]pyrimidin-3-one. $^1$H-NMR (400 MHz, CDCl$_3$) δ: 8.95 (1H, s), 7.91 (tH, t, J=8.0 Hz), 7.76 (1H, d, J=7.3 Hz), 7.40 (1H, dd, J=7.8, 1.0 Hz), 5.70 (1H, ddt, J=17.1, 10.2, 6.3 Hz), 5.06 (1H, dd, J=10.2, 1.0 Hz), 4.93 (1H, dd, J=17.1, 1.2 Hz), 4.81 (2H, d, J=6.3 Hz), 2.59 (4H, s), 1.59 (6H, s). ESI-MS Found: m/z[M+H]+: 358.

Into a 50-mL round-bottom flask, was placed a solution of 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (50.0 mg, 0.14 mmol, 1.00 equiv, ordered from BePharm Ltd.) in toluene (2 mL), MCPBA (24.0 mg, 1.00 equiv). The resulting solution was stirred for 0.5 h at room temperature. Then DIEA (54.0 mg, 0.42 mmol, 3.00 equiv), 1-(1-methylpiperidin-4-yl)-1H-pyrazol-4-amine (30.0 mg, 0.17 mmol, 1.20 equiv) was added. The resulting solution was stirred for 2 h at room temperature. The resulting mixture was concentrated under vacuum. The crude product was purified by Prep-HPLC with the following conditions (SHIMADZU (HPLC-10)): Column, X Bridge Prep C18 OBD Column 19*150 mm 5 um C-0013; mobile phase, A: Water (10 mmon/L NH$_4$HCO$_3$); B: ACN (6 min in 31% B, 20 mL/min); Detector, 254 nm. This resulted in 16.3 mg (19%) of 1-[6-(2-hydroxypropan-2-yl)pyridin-2-yl]-6-[[11-(1-methylpiperidin-4-yl)-1H-pyrazol-4-yl]amino]-2-(prop-2-en-1-yl)-1H,2H,3H-pyrazolo [3,4-d]pyrimidin-3-one as a off-white solid. LC-MS-PH-PHNW-3-2-0 (ES, m/z): [M+H]$^+$: 490. H-NMR-PH-PHNW-3-2-0 (300 MHz, CDCl$_3$, ppm): δ 8.85 (bs, 1H), 8.80-7.82 (m, 2H), 7.74-7.71 (m, 1H), 7.62-7.56 (m, 2H), 7.45-7.42 (m, 1H), 5.77-5.66 (m, 1H), 5.06 (d, J=9.9 Hz, 1H), 4.97-4.91 (m, 1H), 4.73 (d, J=6.3 Hz, 2H), 4.19 (bs, 1H), 3.11-3.08 (m, 2H), 2.44 (s, 3H), 2.25 (br, 4H), 2.10 (br, 3H), 1.61 (s, 6H).

Example 2: Preparation of 1-[6-(2-hydroxypropan-2-yl)pyridin-2-yl]-2-(prop-2-en-1-yl)-6-([1-[1-(propan-2-yl)piperidin-4-yl]-1H-pyrazol-4-yl]amino)-1H,2H,3H-pyrazolo [3,4-d]pyrimidin-3-one Hydrochloride Synthesis of N-(1, 3-dioxo-2,3-dihydro-1H-isoindol-2-yl)(tert-butoxy)formamide: Into a 5000-mL 4-necked round-bottom flask, was placed (tert-butoxy)carbohydrazide (148 g, 1.12 mol, 1.00 equiv), 1,3-dihydro-2-benzofuran-1,3-dione (132 g, 891.20 mmol, 1.00 equiv), toluene (3000 mL). The resulting solution was heated for 48 h under reflux and water separation. The resulting mixture was cooled to 0° C. with an ice/salt bath. The solids were collected by filtration. The filter cake was washed with 1×200 mL of toluene. This resulted in 200 g (68%) of N-(1, 3-dioxo-2,3-dihydro-1H-isoindol-2-yl)(tert-butoxy)formamide as a white solid. LC-MS (ES, m/z): M+1=412$^+$, $^1$H-NMR (300 MHz, CDCl$_3$, ppm): δ 7.98-7.91 (m, 4H), 1.45 (s, 9H).

Synthesis of N-(1,3-dioxo-2,3-dihydro-1H-isoindol-2-yl)-N-(prop-2-en-1-yl)(tert-butoxy)formamide: Into a 3000-mL 4-necked round-bottom flask, was placed N-(1,3-dioxo-2,3-dihydro-1H-isoindol-2-yl)(tert-butoxy)formamide (210 g, 800.73 mmol, 1.00 equiv), BnEt$_3$NCl (20 g, 87.72 mmol, 0.10 equiv), K$_2$CO$_3$ (220 g, 1.58 mol, 2.00 equiv), acetonitrile (2000 mL). This was followed by the addition of 3-bromoprop-1-ene (200 g, 1.65 mol, 2.00 equiv) dropwise with stirring. The resulting solution was stirred overnight at room temperature. The mixture was then quenched by the addition of 100 mL of water. The resulting mixture was concentrated under vacuum. The solids were collected by filtration. The crude product was applied onto a silica gel column with PE/EA (20:1-3:1). This resulted in 100 g (41%) of N-(1,3-dioxo-2,3-dihydro-1H-isoindol-2-yl)-N-(prop-2-en-1-yl)(tert-butoxy)formamide as a white solid. LC-MS (ES, m/z): M+1=303, $^1$H-NMR-PH-PHNW-3-5-2 (300 MHz, CDCl$_3$, ppm): δ 7.98-7.91 (m, 4H), 1.45 (s, 9H).

Synthesis of (tert-butoxy)-N-(prop-2-en-1-yl)carbohydrazide: Into a 2000-mL 4-necked round-bottom flask, was placed N-(1, 3-dioxo-2, 3-dihydro-1H-isoindol-2-yl)-N-(prop-2-en-1-yl)(tert-butoxy)formamide (100 g, 330.77 mmol, 1.00 equiv), oxolane (1000 mL). This was followed by the addition of methylhydrazine (40%) (200 mL, 5.00 equiv) dropwise with stirring at 0° C. The resulting solution was stirred overnight at room temperature. The solids were filtered out. The filtrate was concentrated under vacuum. The residue was applied onto a silica gel column with PE/EA (10:1-1:1) (The silica gel was basified with Et$_3$N). This resulted in 35 g (61%) of (tert-butoxy)-N-(prop-2-en-1-yl) carbohydrazide as yellow oil. $^1$H-NMR (300 MHz, CDCl$_3$, ppm): δ 5.84-5.73 (m, 1H), 5.11-5.10 (m, 1H), 5.08-5.05 (m, 1H), 4.45 (s, 2H), 3.86-3.83 (m, 2H), 1.40 (s, 9H).

Synthesis of ethyl 4-([[(tert-butoxy) carbonyl](prop-2-en-1-yl)amino]amino)-2-(methylsulfanyl)pyrimidine-5-carboxylate: Into a 2000-mL 4-necked round-bottom flask purged and maintained with an inert atmosphere of nitrogen, was placed (tert-butoxy)-N-(prop-2-en-1-yl)carbohydrazide (35 g, 203.22 mmol, 1.00 equiv), DIEA (65.5 g, 506.81 mmol, 2.50 equiv), ethyl 4-chloro-2-(methylsulfanyl)pyrimidine-5-carboxylate (47.35 g, 203.49 mmol, 1.00 equiv), oxolane (1000 mL). The resulting solution was heated to reflux for 48 h in an oil bath. The resulting mixture was cooled to 20° C. with a water bath. The solids were filtered out. The filtrate was concentrated under vacuum. The residue was diluted with 500 mL of water. The resulting solution was extracted with 2×500 mL of ethyl acetate and the organic layers combined. The mixture was washed with 3×200 mL of water, 3×200 mL of brine. The mixture was dried over anhydrous sodium sulfate and concentrated under vacuum. This resulted in 50 g (67%) of ethyl 4-([[(tert-butoxy) carbonyl](prop-2-en-1-yl)amino]amino)-2-(methylsulfanyl)pyrimidine-5-carboxylate as yellow oil. LC-MS (ES, m/z): M+1=369

Synthesis of ethyl 2-(methylsulfanyl)-4-[2-(prop-2-en-1-yl) hydrazin-1-yl]pyrimidine-5-carboxylate: Into a 1000-mL 3-necked round-bottom flask, was placed ethyl 4-([[(tert-butoxy) carbonyl](prop-2-en-1-yl)amino]amino)-2-(methylsulfanyl)pyrimidine-5-carboxylate (50 g, 135.70 mmol, 1.00 equiv), dichloromethane (500 mL). This was followed by the addition of trifluoroacetic acid (90 mL) dropwise with stirring at 0° C. The resulting solution was stirred overnight at room temperature. The resulting mixture was concentrated under vacuum. This resulted in 50 g (crude) of ethyl 2-(methylsulfanyl)-4-[2-(prop-2-en-1-yl) hydrazin-1-yl]pyrimidine-5-carboxylate as a yellow solid. LC-MS (ES, m/z): M+1=269.

Synthesis of 6-(methylsulfanyl)-2-(prop-2-en-1-yl)-1H, 2H, 3H-pyrazolo [3,4-d]pyrimidin-3-one: Into a 2000-mL 4-necked round-bottom flask, was placed ethyl 2-(methylsulfanyl)-4-[2-(prop-2-en-1-yl) hydrazin-1-yl] pyrimidine-5-carboxylate (50 g, 186.33 mmol, 1.00 equiv), ethanol (1000 mL). This was followed by the addition of aqueous NaOH (6 N) (100 mL) dropwise with stirring at 0° C. The resulting solution was stirred for 1 h at room temperature. The resulting mixture was concentrated under vacuum. The residue was applied onto a silica gel column with dichloromethane/methanol (10:1). This resulted in 20 g (48%) of 6-(methylsulfanyl)-2-(prop-2-en-1-yl)-1H, 2H, 3H-pyrazolo [3,4-d]pyrimidin-3-one as a yellow solid. LC-MS (ES, m/z): M+1=223, $^{1}$H-NMR (300 MHz, CDCl$_3$, ppm): δ 8.65 (s, 1H), 5.93-5.80 (m, 1H), 5.17-5.05 (m, 1H), 4.63-4.60 (m, 2H), 1.291.23 (m, 3H).

Synthesis of 1-[6-(2-hydroxypropan-2-yl) pyridin-2-yl]-6-(methylsulfanyl)-2-(prop-2-en-1-yl)-1H,2H,3H-pyrazolo [3,4-d]pyrimidin-3-one: Into a 1000-mL 3-necked round-bottom flask, was placed 6-(methylsulfanyl)-2-(prop-2-en-1-yl)-1H,2H,3H-pyrazolo[3,4-d]pyrimidin-3-one (20 g, 89.98 mmol, 1.00 equiv), 2-(6-bromopyridin-2-yl)propan-2-ol (24 g, 111.07 mmol, 1.23 equiv), 1,4-dioxane (500 mL), iodocopper (17.1 g, 89.79 mmol, 1.0 equiv), K$_2$CO$_3$ (17.1 g, 122.83 mmol, 1.37 equiv). This was followed by the addition of methyl [2-(methylamino) ethyl] amine (10.8 mL) dropwise with stirring. The resulting solution was stirred overnight at 95° C. in an oil bath. The resulting mixture was cooled to room temperature. The mixture was then quenched by the addition of 100 mL of water. The resulting mixture was concentrated under vacuum. The residue was extracted with 3×500 mL of ethyl acetate and the organic layers combined. The residue was applied onto a silica gel column with ethyl acetate/petroleum ether (1:5-1:3). This resulted in 15 g (47%) of 1-[6-(2-hydroxypropan-2-yl) pyridin-2-yl]-6-(methylsulfanyl)-2-(prop-2-en-1-yl)-1H,2H,3H-pyrazolo[3,4-d]pyrimidin-3-one as a white solid. LC-MS (ES, m/z): M+1=358

Synthesis of 2-(6-bromopyridin-2-yl)propan-2-ol: Into a 2000-mL 4-necked round-bottom flask purged and maintained with an inert atmosphere of nitrogen, was placed methyl 6-bromopyridine-2-carboxylate (43.2 g, 199.97 mmol, 1.00 equiv), tetrahydrofuran (700 mL). This was followed by the addition of bromo(methyl)magnesium (150 mL) dropwise with stirring at 0° C. The resulting solution was stirred overnight at room temperature. The mixture was then quenched by the addition of 200 mL of water. The resulting solution was extracted with 3×200 mL of ethyl acetate and the organic layers combined. The resulting mixture was washed with 2×200 mL of brine. The mixture was dried over anhydrous sodium sulfate and concentrated under vacuum. This resulted in 35 g (81%) of 2-(6-bromopyridin-2-yl)propan-2-ol as yellow oil.

Synthesis of 4-(4-nitro-1H-pyrazol-1-yl)-1-(propan-2-yl) piperidine: Into a 100-mL 3-necked round-bottom flask purged and maintained with an inert atmosphere of nitrogen, was placed 4-nitro-1H-pyrazole (565 mg, 4.997 mmol, 1 equiv), 1-(propan-2-yl)piperidin-4-ol (715.67 mg, 4.997 mmol, 1.00 equiv), PPh$_3$ (1572.66 mg, 5.996 mmol, 1.2 equiv), THF (50 mL). This was followed by the addition of DEAD (1131.24 mg, 6.496 mmol, 1.3 equiv) at 0° C. The resulting solution was stirred for overnight at room temperature. The reaction was then quenched by the addition of 50 mL of water. The resulting solution was extracted with 2×100 mL of ethyl acetate concentrated. The residue was applied onto a silica gel column with ethyl acetate/petroleum ether (3:2). The collected fractions were combined and concentrated. This resulted in 670 mg (56.27%) of 4-(4-nitro-1H-pyrazol-1-yl)-1-(propan-2-yl)piperidine as a white solid. LC-MS (ES, m/z): 239[M+1]$^+$ Synthesis of 1-[1-(propan-2-yl) piperidin-4-yl]-1H-pyrazol-4-amine: Into a 100-mL round-bottom flask, was placed 4-(4-nitro-1H-pyrazol-1-yl)-1-(propan-2-yl)piperidine (670 mg, 2.812 mmol, 1 equiv), MeOH (20 mg, 0.624 mmol, 0.22 equiv), Pd/C (100 mg, 0.940 mmol, 0.33 equiv), H$_2$. The resulting solution was stirred for overnight at room temperature. The solids were filtered out. The resulting mixture was concentrated. The residue was applied onto a silica gel column with dichloromethane/methanol (10:1). The collected fractions were combined and concentrated. This resulted in 70 mg (11.95%) of 1-[1-(propan-2-yl) piperidin-4-yl]-1H-pyrazol-4-amine as a white solid. LC-MS (ES, m/z): 209[M+1]$^+$ Synthesis of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (40 mg, 0.112 mmol, 1 equiv), toluene (2 mL), 0.022 mmol, 0.19 equiv), m-CPBA (19.31 mg, 0.112 mmol, 1.00 equiv). The resulting solution was stirred for 30 min at room temperature. The resulting mixture was concentrated. This resulted in 20 mg (48%) of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one as a white solid. LC-MS (ES, m/z): 374[M+1]$^+$ Synthesis of 1-[6-(2-hydroxypropan-2-yl)pyridin-2-yl]-2-(prop-2-en-1-yl)-6-([1-[1-(propan-2-yl)piperidin-4-yl]-1H-pyrazol-4-yl]amino)-1H,2H,3H-pyrazolo[3,4-d]pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (42 mg, 0.118 mmol, 1 equiv), toluene (2 mL), 1-[1-(propan-2-yl)piperidin-4-yl]-1H-pyrazol-4-amine (29.37 mg, 0.141 mmol, 1.20 equiv), DIEA (45.56 mg, 0.353 mmol, 3 equiv). The resulting solution was stirred for 2 hr at room temperature. The resulting mixture was concentrated. The crude product (30 mg) was purified by Prep-HPLC with the following conditions (2#SHIMADZU): Column: atlatis HILTC OBD 19*150 mm*5 um; mobile phase, Phase A: Water (0.1% FA) Phase B: ACN B: 2%-22% 7 min; Detector, UV 220 nm.

This resulted in 5.2 mg (7.99%) of 1-[6-(2-hydroxypropan-2-yl)pyridin-2-yl]-2-(prop-2-en-1-yl)-6-([1-[1-(propan-2-yl)piperidin-4-yl]-1H-pyrazol-4-yl]amino)-1H,2H,3H-pyrazolo[3,4-d]pyrimidin-3-one hydrochloride as a yellow solid. LC-MS (ES, m/z): 518[M+1]$^+$, $^1$H-NMR (300 MHz, DMSO-$d_6$) δ 8.84 (d, J=23.1 Hz, 1H), 8.17-7.88 (m, 2H), 7.83-7.55 (m, 3H), 5.68-5.59 (m, 1H), 5.07-4.92 (m, 1H), 4.79 (d, J=17.1 Hz, 1H), 4.63 (d, J=6.0 Hz, 2H), 4.46 (s, 1H), 3.59-3.38 (m, 3H), 3.22-3.15 (m, 2H), 2.50-2.19 (m, 4H), 1.45 (s, 6H), 1.30-1.25 (m, 6H).

Example 3: Preparation of 6-([1-[1-(4,4-difluorocyclohexyl)piperidin-4-yl]-1H-pyrazol-4-yl]amino)-1-[6-(2-hydroxypropan-2-yl)pyridin-2-yl]-2-(prop-2-en-1-yl)-1H,2H,3H-pyrazolo[3,4-d]pyrimidin-3-one Hydrochloride Synthesis of N-(1, 3-dioxo-2,3-dihydro-1H-isoindol-2-yl)(tert-butoxy)formamide: Into a 5000-mL 4-necked round-bottom flask, was placed (tert-butoxy)carbohydrazide (148 g, 1.12 mol, 1.00 equiv), 1,3-dihydro-2-benzofuran-1,3-dione (132 g, 891.20 mmol, 1.00 equiv), toluene (3000 mL). The resulting solution was heated for 48 h under reflux and water separation. The resulting mixture was cooled to 0° C. with an ice/salt bath. The solids were collected by filtration. The filter cake was washed with 1×200 mL of toluene. This resulted in 200 g (68%) of N-(1, 3-dioxo-2,3-dihydro-1H-isoindol-2-yl)(tert-butoxy)formamide as a white solid. LC-MS (ES, m/z): M+1=412$^+$, $^1$H-NMR (300 MHz, CDCl$_3$, ppm): δ 7.98-7.91 (m, 4H), 1.45 (s, 9H).

Synthesis of N-(1,3-dioxo-2,3-dihydro-1H-isoindol-2-yl)-N-(prop-2-en-1-yl)(tert-butoxy)formamide: Into a 3000-mL 4-necked round-bottom flask, was placed N-(1,3-dioxo-2,3-dihydro-1H-isoindol-2-yl)(tert-butoxy)formamide (210 g, 800.73 mmol, 1.00 equiv), BnEt$_3$NCl (20 g, 87.72 mmol, 0.10 equiv), K$_2$CO$_3$ (220 g, 1.58 mol, 2.00 equiv), acetonitrile (2000 mL). This was followed by the addition of 3-bromoprop-1-ene (200 g, 1.65 mol, 2.00 equiv) dropwise with stirring. The resulting solution was stirred overnight at room temperature. The mixture was then quenched by the addition of 100 mL of water. The resulting mixture was concentrated under vacuum. The solids were collected by filtration. The crude product was applied onto a silica gel column with PE/EA (20:1-3:1). This resulted in 100 g (41%) of N-(1,3-dioxo-2,3-dihydro-1H-isoindol-2-yl)-N-(prop-2-en-1-yl)(tert-butoxy)formamide as a white solid. LC-MS (ES, m/z): M+1=303, $^1$H-NMR-PH-PHNW-3-5-2 (300 MHz, CDCl$_3$, ppm): δ 7.98-7.91 (m, 4H), 1.45 (s, 9H).

Synthesis of (tert-butoxy)-N-(prop-2-en-1-yl)carbohydrazide: Into a 2000-mL 4-necked round-bottom flask, was placed N-(1, 3-dioxo-2, 3-dihydro-1H-isoindol-2-yl)-N-(prop-2-en-1-yl)(tert-butoxy)formamide (100 g, 330.77 mmol, 1.00 equiv), oxolane (1000 mL). This was followed by the addition of methylhydrazine (40%) (200 mL, 5.00 equiv) dropwise with stirring at 0° C. The resulting solution was stirred overnight at room temperature. The solids were filtered out. The filtrate was concentrated under vacuum. The residue was applied onto a silica gel column with PE/EA (10:1-1:1) (The silica gel was basified with Et$_3$N). This resulted in 35 g (61%) of (tert-butoxy)-N-(prop-2-en-1-yl)carbohydrazide as yellow oil. $^1$H-NMR (300 MHz, CDCl$_3$, ppm): δ 5.84-5.73 (m, 1H), 5.11-5.10 (m, 1H), 5.08-5.05 (m, 1H), 4.45 (s, 2H), 3.86-3.83 (m, 2H), 1.40 (s, 9H).

Synthesis of ethyl 4-([[(tert-butoxy) carbonyl](prop-2-en-1-yl)amino]amino)-2-(methylsulfanyl)pyrimidine-5-carboxylate: Into a 2000-mL 4-necked round-bottom flask purged and maintained with an inert atmosphere of nitrogen, was placed (tert-butoxy)-N-(prop-2-en-1-yl)carbohydrazide (35 g, 203.22 mmol, 1.00 equiv), DIEA (65.5 g, 506.81 mmol, 2.50 equiv), ethyl 4-chloro-2-(methylsulfanyl)pyrimidine-5-carboxylate (47.35 g, 203.49 mmol, 1.00 equiv), oxolane (1000 mL). The resulting solution was heated to reflux for 48 h in an oil bath. The resulting mixture was cooled to 20° C. with a water bath. The solids were filtered out. The filtrate was concentrated under vacuum. The residue was diluted with 500 mL of water. The resulting solution was extracted with 2×500 mL of ethyl acetate and the organic layers combined. The mixture was washed with 3×200 mL of water, 3×200 mL of brine. The mixture was dried over anhydrous sodium sulfate and concentrated under vacuum. This resulted in 50 g (67%) of ethyl 4-([[(tert-butoxy) carbonyl](prop-2-en-1-yl)amino]amino)-2-(methylsulfanyl)pyrimidine-5-carboxylate as yellow oil. LC-MS (ES, m/z): M+1=369

Synthesis of ethyl 2-(methylsulfanyl)-4-[2-(prop-2-en-1-yl) hydrazin-1-yl]pyrimidine-5-carboxylate: Into a 1000-mL 3-necked round-bottom flask, was placed ethyl 4-([[(tert-butoxy) carbonyl](prop-2-en-1-yl)amino]amino)-2-(methylsulfanyl)pyrimidine-5-carboxylate (50 g, 135.70 mmol, 1.00 equiv), dichloromethane (500 mL). This was followed by the addition of trifluoroacetic acid (90 mL) dropwise with stirring at 0° C. The resulting solution was stirred overnight at room temperature. The resulting mixture was concentrated under vacuum. This resulted in 50 g (crude) of ethyl 2-(methylsulfanyl)-4-[2-(prop-2-en-1-yl) hydrazin-1-yl]pyrimidine-5-carboxylate as a yellow solid. LC-MS (ES, m/z): M+1=269.

Synthesis of 6-(methylsulfanyl)-2-(prop-2-en-1-yl)-1H,2H, 3H-pyrazolo [3,4-d]pyrimidin-3-one: Into a 2000-mL 4-necked round-bottom flask, was placed ethyl 2-(methylsulfanyl)-4-[2-(prop-2-en-1-yl) hydrazin-1-yl] pyrimidine-5-carboxylate (50 g, 186.33 mmol, 1.00 equiv), ethanol (1000 mL). This was followed by the addition of aqueous NaOH (6 N) (100 mL) dropwise with stirring at 0° C. The resulting solution was stirred for 1 h at room temperature. The resulting mixture was concentrated under vacuum. The residue was applied onto a silica gel column with dichloromethane/methanol (10:1). This resulted in 20 g (48%) of 6-(methylsulfanyl)-2-(prop-2-en-1-yl)-1H, 2H, 3H-pyrazolo [3,4-d]pyrimidin-3-one as a yellow solid. LC-MS (ES, m/z): M+1=223, $^1$H-NMR (300 MHz, CDCl$_3$, ppm): δ 8.65 (s, 1H), 5.93-5.80 (m, 1H), 5.17-5.05 (m, 1H), 4.63-4.60 (m, 2H), 1.291.23 (m, 3H).

Synthesis of 1-[6-(2-hydroxypropan-2-yl) pyridin-2-yl]-6-(methylsulfanyl)-2-(prop-2-en-1-yl)-1H,2H,3H-pyrazolo [3,4-d]pyrimidin-3-one: Into a 1000-mL 3-necked round-bottom flask, was placed 6-(methylsulfanyl)-2-(prop-2-en-1-yl)-1H,2H,3H-pyrazolo[3,4-d]pyrimidin-3-one (20 g, 89.98 mmol, 1.00 equiv), 2-(6-bromopyridin-2-yl)propan-2-ol (24 g, 111.07 mmol, 1.23 equiv), 1,4-dioxane (500 mL), iodocopper (17.1 g, 89.79 mmol, 1.0 equiv), K$_2$CO$_3$ (17.1 g, 122.83 mmol, 1.37 equiv). This was followed by the addition of methyl [2-(methylamino) ethyl] amine (10.8 mL) dropwise with stirring. The resulting solution was stirred overnight at 95° C. in an oil bath. The resulting mixture was cooled to room temperature. The mixture was then quenched by the addition of 100 mL of water. The resulting mixture was concentrated under vacuum. The residue was extracted with 3×500 mL of ethyl acetate and the organic layers combined. The residue was applied onto a silica gel column with ethyl acetate/petroleum ether (1:5-1:3). This resulted in 15 g (47%) of 1-[6-(2-hydroxypropan-2-yl) pyridin-2-yl]-6-

(methylsulfanyl)-2-(prop-2-en-1-yl)-1H,2H,3H-pyrazolo[3,4-d]pyrimidin-3-one as a white solid. LC-MS (ES, m/z): M+1=358

Synthesis of 2-(6-bromopyridin-2-yl)propan-2-ol: Into a 2000-mL 4-necked round-bottom flask purged and maintained with an inert atmosphere of nitrogen, was placed methyl 6-bromopyridine-2-carboxylate (43.2 g, 199.97 mmol, 1.00 equiv), tetrahydrofuran (700 mL). This was followed by the addition of bromo(methyl)magnesium (150 mL) dropwise with stirring at 0° C. The resulting solution was stirred overnight at room temperature. The mixture was then quenched by the addition of 200 mL of water. The resulting solution was extracted with 3×200 mL of ethyl acetate and the organic layers combined. The resulting mixture was washed with 2×200 mL of brine. The mixture was dried over anhydrous sodium sulfate and concentrated under vacuum. This resulted in 35 g (81%) of 2-(6-bromopyridin-2-yl)propan-2-ol as yellow oil.

Synthesis of tert-butyl 4-(4-nitro-1H-pyrazol-1-yl) mpiperidine-1-carboxylate: Into a 500-mL 3-necked round-bottom flask purged and maintained with an inert atmosphere of nitrogen, was placed 4-nitro-1H-pyrazole (10.17 g, 89.940 mmol, 1 equiv), tert-butyl 4-hydroxypiperidine-1-carboxylate (18.10 g, 0.090 mmol, 1 equiv), PPh$_3$ (28.31 g, 0.108 mmol, 1.2 equiv), THF (300 mL). This was followed by the addition of DEAD (20.36 g, 0.117 mmol, 1.3 equiv) dropwise with stirring at −15° C. in 20 min. The resulting solution was stirred for overnight at room temperature. The reaction was then quenched by the addition of 300 mL of water. The resulting solution was extracted with 2×300 mL of ethyl acetate concentrated. The residue was applied onto a silica gel column with ethyl acetate/petroleum ether (9:1). The collected fractions were combined and concentrated. This resulted in 25.8 g (96.81%) of tert-butyl 4-(4-nitro-1H-pyrazol-1-yl) mpiperidine-1-carboxylate as a white solid. $^1$H NMR (300 MHz, DMSO-d6, 300 ppm): δ 8.96 (s, 1H), 8.28 (s, 1H), 4.47-4.43 (m, 1H), 4.17-3.90 (m, 2H), 2.91 (s, 2H), 2.11-2.01 (m, 2H), 1.82-1.75 (m, 2H), 1.42 (s, 9H)

Synthesis of 4-(4-nitro-1H-pyrazol-1-yl)piperidine: Into a 100-mL round-bottom flask, was placed tert-butyl 4-(4-nitro-1H-pyrazol-1-yl) piperidine-1-carboxylate (10 g, 1 equiv), HCl/dioxane (60 mL). The resulting solution was stirred for 3 hr at room temperature. The resulting mixture was concentrated. The reaction was then quenched by the addition of 100 mL of water. The pH value of the solution was adjusted to 8 with NaHCO$_3$ (2 mol/L). The resulting solution was extracted with 3×200 mL of ethyl acetate concentrated. The residue was applied onto a silica gel column with dichloromethane/methanol (10:1). The collected fractions were combined and concentrated. This resulted in 4.2 g of 4-(4-nitro-1H-pyrazol-1-yl)piperidine as a white solid. LC-MS: (ES, m/z): 197[M+1]$^+$ Synthesis of 1-(4,4-difluorocyclohexyl)-4-(4-nitro-1H-pyrazol-1-yl)piperidine: Into a 100-mL round-bottom flask, was placed 4,4-difluorocyclohexan-1-one (622 mg, 4.637 mmol, 1 equiv), 4-(4-nitro-1H-pyrazol-1-yl)piperidine (909.91 mg, 4.637 mmol, 1.00 equiv), MeOH (20 mL), ZnCl$_2$ (1390.73 mg, 10.20 mmol, 2.2 equiv), NaBH$_3$CN (641.14 mg, 10.20 mmol, 2.2 equiv). The resulting solution was stirred for overnight at 80° C. in an oil bath. The resulting mixture was concentrated. The reaction was then quenched by the addition of 50 mL of water. The solids were filtered out. The resulting solution was extracted with 3×50 mL of ethyl acetate concentrated. The residue was applied onto a silica gel column with dichloromethane/methanol (10:1). The collected fractions were combined and concentrated. This resulted in 600 mg (41.16%) of 1-(4,4-difluorocyclohexyl)-4-(4-nitro-1H-pyrazol-1-yl)piperidine as a white solid. LC-MS (ES, m/z): 315[M+1]$^+$ Synthesis of 1-[1-(4, 4-difluorocyclohexyl) piperidin-4-yl]-1H-pyrazol-4-amine: Into a 100-mL round-bottom flask, was placed 1-(4, 4-difluorocyclohexyl)-4-(4-nitro-1H-pyrazol-1-yl) piperidine (314 mg, 0.999 mmol, 1 equiv), MeOH (20 mL), Pd/C (100 mg, 0.940 mmol, 0.94 equiv), H$_2$. The resulting solution was stirred for overnight at room temperature. The solids were filtered out. The resulting mixture was concentrated. This resulted in 20 mg (7.04%) of 1-[1-(4, 4-difluorocyclohexyl) piperidin-4-yl]-1H-pyrazol-4-amine as a white solid. LC-MS (ES, m/z): 285[M+1]$^+$ Synthesis of 6-([1-[1-(4,4-difluorocyclohexyl)piperidin-4-yl]-1H-pyrazol-4-yl]amino)-1-[6-(2-hydroxypropan-2-yl)pyridin-2-yl]-2-(prop-2-en-1-yl)-1H,2H,3H-pyrazolo[3,4-d]pyrimidin-3-one hydrochloride: Into a 8-mL vial, was placed 1-[6-(2-hydroxypropan-2-yl)pyridin-2-yl]-6-methanesulfinyl-2-(prop-2-en-1-yl)-1H,2H,3H-pyrazolo[3,4-d]pyrimidin-3-one (20 mg, 0.054 mmol, 1 equiv), toluene (2 mL), 1-[1-(4,4-difluorocyclohexyl)piperidin-4-yl]-1H-pyrazol-4-amine (15.23 mg, 0.054 mmol, 1.00 equiv), DIEA (20.77 mg, 0.161 mmol, 3 equiv). The resulting solution was stirred for 2 hr at room temperature. The resulting mixture was concentrated. The crude product (20 mg) was purified by Prep-HPLC with the following conditions: Column, X-bridge RP18; mobile phase, 0.05% FA in water and CH$_3$CN (45% CH$_3$CN up to 60% in 5 min); Detector, UV 220 nm. This resulted in 4.9 mg (14.52%) of 6-([1-[1-(4,4-difluorocyclohexyl)piperidin-4-yl]-1H-pyrazol-4-yl]amino)-1-[6-(2-hydroxypropan-2-yl)pyridin-2-yl]-2-(prop-2-en-1-yl)-1H,2H,3H-pyrazolo[3,4-d]pyrimidin-3-one hydrochloride as a white solid. LC-MS (ES, m/z): 594[M+1]$^+$, $^1$H NMR (300 MHz, DMSO-d6, ppm) δ 8.82 (s, 1H), 8.20-7.90 (m, 2H), 7.76 (d, J=8.1 Hz, 1H), 7.71-7.57 (m, 2H), 5.77-5.57 (m, 1H), 5.00 (d, J=10.5 Hz, 1H), 4.80 (d, J=17.1 Hz, 1H), 4.64 (d, J=6.0 Hz, 3H), 3.25 (s, 4H), 2.3-2.09 (m, 10H), 1.72 (s, 2H), 1.46 (s, 6H).

Example 4: Preparation of 6-[(1-[4-[4-(cyclopropylmethyl)piperazin-1-yl]cyclohexyl]-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one Synthesis of 1-(cyclopropylmethyl)-4-[1, 4-dioxaspiro [4.5] decan-8-yl]piperazine: Into a 250-mL round-bottom flask, was placed 1, 4-dioxaspiro [4.5] decan-8-one (2.75 g, 0.018 mmol, 1.20 equiv), 1-(cyclopropylmethyl)piperazine (2.06 g, 14.690 mmol, 1 equiv), HOAc (0.88 g, 0.015 mmol, 1.00 equiv), DCM (100 mL). This was followed by the addition of NaBH(OAc)$_3$ (3.74 g, 0.018 mmol, 1.20 equiv) at 0 degrees C. The resulting solution was stirred for overnight at room temperature. The pH value of the solution was adjusted to 8 with NaHCO$_3$ (2 mol/L). The resulting solution was extracted with 3×100 mL of dichloromethane concentrated. The residue was applied onto a silica gel column with dichloromethane/methanol (10:1). The collected fractions were combined and concentrated. This resulted in 2.9 g (70.40%) of 1-(cyclopropylmethyl)-4-[1, 4-dioxaspiro [4.5] decan-8-yl] piperazine as colorless oil. LC-MS (ES, m/z): 281[M+1]$^+$ Synthesis of 4-[4-(cyclopropylmethyl) piperazin-1-yl] cyclohexan-1-one: Into a 50-mL round-bottom flask, was placed 1-(cyclopropylmethyl)-4-[1, 4-dioxaspiro [4.5] decan-8-yl] piperazine (780 mg, 2.782 mmol, 1 equiv), THF (20 mL), HCl (6M) (2 mL, 0.055 mmol, 0.02 equiv). The resulting solution was stirred for overnight at room temperature. The pH value of the solution was adjusted to 8 with NaHCO$_3$ (2 mol/L). The resulting solution was extracted with 3×20 mL of dichloromethane. The organic layer was dried over anhydrous sodium sulfate and concentrated under vacuum. The residue was applied onto a silica gel column with dichloromethane/methanol (10:1). The collected fractions were combined and concentrated. This resulted in 620 mg (94.30%) of 4-[4-(cyclopropylmethyl) piperazin-1-yl] cyclohexan-1-one as light yellow oil. LC-MS-2: (ES, m/z): 237[M+1]$^+$ Synthesis of 4-[4-(cyclopropylmethyl) piperazin-1-yl] cyclohexan-1-ol: Into a 100-mL round-bottom flask, was placed 4-[4-(cyclopropylmethyl) piperazin-1-yl] cyclohexan-1-one (620 mg, 2.623 mmol, 1 equiv), MeOH (20 mL, 0.624 mmol, 0.24 equiv). This was followed by the addition of NaBH$_4$ (297.72 mg, 7.869 mmol, 3.00 equiv) at 0 degrees C. The resulting solution was stirred for overnight at room temperature. The reaction was then quenched by the addition of 10 mL of water. The resulting solution was extracted with 3×20 mL of ethyl acetate. The organic layer was dried over anhydrous sodium sulfate and concentrated under vacuum. This resulted in 500 mg (crude) of 4-[4-(cyclopropylmethyl) piperazin-1-yl] cyclohexan-1-ol as colorless oil. LC-MS-3: (ES, m/z): 239[M+1]$^+$ Synthesis of 4-[4-(cyclopropylmethyl) piperazin-1-yl] cyclohexyl methanesulfonate: Into a 8-mL vial, was placed 4-[4-(cyclopropylmethyl) piperazin-1-yl]cyclohexan-1-ol (106 mg, 0.445 mmol, 1 equiv), DCM (4 mL), TEA (89.99 mg, 0.889 mmol, 2 equiv). This was followed by the addition of methanesulfonyl chloride (56.03 mg, 0.489 mmol, 1.10 equiv) at 0 degrees C. The resulting solution was stirred for overnight at room temperature. The reaction was then quenched by the addition of 4 mL of water. The resulting solution was extracted with 3×4 mL of dichloromethane concentrated. This resulted in 100 mg (crude) of 4-[4-(cyclopropylmethyl) piperazin-1-yl] cyclohexyl methanesulfonate as light yellow oil. LC-MS-4 (ES, m/z): 222 [M+1]$^+$ Synthesis of 1-(cyclopropylmethyl)-4-[4-(4-nitro-1H-pyrazol-1-yl) cyclohexyl]piperazine: Into a 50-mL round-bottom flask, was placed 4-nitro-1H-pyrazole (179 mg, 1.583 mmol, 1 equiv), DMF (20 mL). This was followed by the addition of NaH (113.97 mg, 4.749 mmol, 3 equiv) at 0 degrees C. To this was added 4-[4-(cyclopropylmethyl) piperazin-1-yl]cyclohexyl methanesulfonate (500.96 mg, 1.583 mmol, 1.00 equiv) at 0 degrees C. The resulting solution was stirred for 3 hr at 100 degrees C. in an oil bath. The reaction was then quenched by the addition of 20 mL of water. The resulting solution was extracted with 3×20 mL of ethyl acetate. The organic layer was dried over anhydrous sodium sulfate and concentrated under vacuum. This resulted in 220 mg (crude) of 1-(cyclopropylmethyl)-4-[4-(4-nitro-1H-pyrazol-1-yl) cyclohexyl]piperazine as a light yellow oil. LC-MS-5 (ES, m/z): 334[M+1]$^+$ Synthesis of 1-[4-[4-(cyclopropylmethyl) piperazin-1-yl] cyclohexyl]-1H-pyrazol-4-amine: Into a 100-mL round-bottom flask, was placed 1-(cyclopropylmethyl)-4-[4-(4-nitro-1H-pyrazol-1-yl) cyclohexyl] piperazine (100 mg, 0.300 mmol, 1 equiv), MeOH (10 mL), Pd/C (50 mg, 0.470 mmol, 1.57 equiv), H$_2$. The resulting solution was stirred for overnight at room temperature. The solids were filtered out. The resulting mixture was concentrated. This resulted in 67 mg (crude) of 1-[4-[4-(cyclopropylmethyl) piperazin-1-yl] cyclohexyl]-1H-pyrazol-4-amine as a white solid. LC-MS-6: (ES, m/z): 304[M+1]$^+$ Synthesis of 6-[(1-[4-[4-(cyclopropylmethyl)piperazin-1-yl]cyclohexyl]-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (50 mg, 0.140 mmol, 1 equiv), toluene (5 mL), 1-[4-[4-(cyclopropylmethyl)piperazin-1-yl]cyclohexyl]-1H-pyrazol-4-amine (50.94 mg, 0.168 mmol, 1.20 equiv), DIEA (54.24 mg, 0.420 mmol, 3 equiv). The resulting solution was stirred for 2 hr at room temperature. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector, UV 254 nm. This resulted in 8.7 mg (10.15%) of 6-[(1-[4-[4-(cyclopropylmethyl)piperazin-1-yl]cyclohexyl]-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one as a white solid. LC-MS-0: (ES, m/z): 613 [M+1]$^+$, $^1$H NMR (300 MHz, Chloroform-d, ppm) δ 8.85 (s, 1H), 7.90-7.85 (m, 1H), 7.74 (d, J=7.8 Hz, 2H), 7.63 (s, 1H), 7.40-7.35 (m, 2H), 5.83-5.60 (m, 1H), 5.06 (d, J=10.2 Hz, 1H), 4.94 (d, J=17.4 Hz, 1H), 4.74 (d, J=6.3 Hz, 2H), 4.09-4.01 (m, 1H), 3.89 (s, 1H), 2.75 (s, 7H), 2.50-2.20 (m, 5H), 2.20-1.95 (m, 3H), 1.89-1.70 (m, 2H), 1.53-1.39 (m, 3H), 1.29 (s, 5H), 0.90 (s, 1H), 0.57 (d, J=7.5 Hz, 2H), 0.13 (d, J=23.4 Hz, 2H).

Example 5: Preparation of 1-[6-(2-hydroxypropan-2-yl)pyridin-2-yl]-2-(prop-2-en-1-yl)-6-([1-[1-(propan-2-yl)-[1,4-bipiperidin]-4-yl]-1H-pyrazol-4-yl]amino)-1H,2H,3H-pyrazolo[3,4-d]pyrimidin-3-one Hydrochloride Synthesis of 1'-isopropyl-4-(4-nitro-1H-pyrazol-1-yl)-1, 4'-bipiperidine: Into a 100-mL round-bottom flask, was placed 4-(4-nitro-1H-pyrazol-1-yl)piperidine (1 g, 5.097 mmol, 1 equiv), 1-(propan-2-yl)piperidin-4-one (0.72 g, 0.005 mmol, 1.00 equiv), MeOH (20 mL), ZnCl$_2$ (1.39 g, 0.010 mmol, 2 equiv), NaBH$_3$CN (0.64 g, 0.010 mmol, 2 equiv). The resulting solution was stirred for overnight at 80° C. in an oil bath. The reaction was then quenched by the addition of 20 mL of water. The solids were filtered out. The resulting mixture was concentrated. The residue was applied onto a silica gel column with dichloromethane/methanol (10:1). The collected fractions were combined and concentrated. This resulted in 900 mg (54.94%) of 1'-isopropyl-4-(4-nitro-1H-pyrazol-1-yl)-1, 4'-bipiperidine as a white solid. LC-MS (ES, m/z): 322[M+1]$^+$ Synthesis of 1-[1-(propan-2-yl)-[1, 4-bipiperidin]-4-yl]-1H-pyrazol-4-amine: Into a 50-mL round-bottom flask, was placed 4-(4-nitro-1H-pyrazol-1-yl)-1-(propan-2-yl)-1, 4-bipiperidine (321 mg, 0.999 mmol, 1 equiv), MeOH (15 mL), Pd/C (100 mg, 0.940 mmol, 0.94 equiv), H$_2$. The resulting solution was stirred for overnight at room temperature. The solids were filtered out. The resulting mixture was concentrated and purification by Pre-TLC. This resulted in 100 mg (34.36%) of 1-[1-(propan-2-yl)-[1, 4-bipiperidin]-4-yl]-1H-pyrazol-4-amine as a white solid. LC-MS (ES, m/z): 292[M+1]$^+$ Synthesis of 1-[6-(2-hydroxypropan-2-yl)pyridin-2-yl]-2-(prop-2-en-1-yl)-6-([1-[1-(propan-2-yl)-[1,4-bipiperidin]-4-yl]-1H-pyrazol-4-yl]amino)-1H,2H,3H-pyrazolo[3,4-d]pyrimidin-3-one hydrochloride: Into a 8-mL vial, was placed 1-[6-(2-hydroxypropan-2-yl)pyridin-2-yl]-6-methanesulfinyl-2-(prop-2-en-1-yl)-1H,2H,3H-pyrazolo[3,4-d]pyrimidin-3-one (40 mg, 0.107 mmol, 1 equiv), m-CPBA (18.48 mg, 0.107 mmol, 1 equiv), toluene (2 mL, 0.022 mmol, 0.20 equiv), The resulting solution was stirred for 2 hr at room temperature. Then added DIEA (41.53 mg, 0.321 mmol, 3 equiv), 1-[1-(propan-2-yl)-[1,4-bipiperidin]-4-yl]-1H-pyrazol-4-amine (37.46 mg, 0.129 mmol, 1.20 equiv) at r.t. The resulting solution was stirred for 2 hr at room temperature. The resulting mixture was concentrated. The crude product (30 mg) was purified by Prep-HPLC with the following conditions: Column, X-bridge RP18; mobile phase, 0.05% FA in water and $CH_3CN$ (45% $CH_3CN$ up to 60% in 5 min); Detector, UV 254 nm. This resulted in 5 mg (7.33%) of 1-[6-(2-hydroxypropan-2-yl)pyridin-2-yl]-2-(prop-2-en-1-yl)-6-([1-[1-(propan-2-yl)-[1,4-bipiperidin]-4-yl]-1H-pyrazol-4-yl]amino)-1H,2H,3H-pyrazolo[3,4-d]pyrimidin-3-one hydrochloride as a white solid. LC-MS (ES, m/z): 601[M+1]$^+$, $^1$H NMR (300 MHz, DMSO-d6, ppm) δ 8.85 (s, 1H), 8.23-7.86 (m, 2H), 7.82-7.54 (m, 3H), 5.70-5.61 (m, 1H), 5.00 (d, J=10.5 Hz, 1H), 4.79 (d, J=17.1 Hz, 1H), 4.71-4.57 (m, 2H), 4.47 (s, 1H), 3.56-3.35 (m, 5H), 3.22 (s, 2H), 3.13-2.91 (m, 2H), 2.31 (d, J=18.0 Hz, 6H), 2.03 (s, 2H), 1.46 (s, 6H), 1.26 (d, J=6.6 Hz, 6H).

Example 6: Preparation of 1-[6-(2-hydroxypropan-2-yl)pyridin-2-yl]-2-(prop-2-en-1-yl)-6-[[1-(propan-2-yl)-1H-pyrazol-4-yl]amino]-1H,2H,3H-pyrazolo[3,4-d]pyrimidin-3-one Synthesis of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (30 mg, 0.084 mmol, 1 equiv), toluene (2 mL, 0.022 mmol, 0.26 equiv), m-CPBA (14.48 mg, 0.084 mmol, 1.00 equiv). The resulting solution was stirred for 2 hr at room temperature. The resulting mixture was concentrated. This resulted in 36.4 mg (116.13%) of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one as a white solid. LC-MS (ES, m/z): 374[M+1]$^+$ Synthesis of 1-[6-(2-hydroxypropan-2-yl)pyridin-2-yl]-2-(prop-2-en-1-yl)-6-[[1-(propan-2-yl)-1H-pyrazol-4-yl]amino]-1H,2H,3H-pyrazolo[3,4-d]pyrimidin-3-one hydrochloride: Into a 8-mL vial, was placed 1-[6-(2-hydroxypropan-2-yl)pyridin-2-yl]-6-methanesulfinyl-2-(prop-2-en-1-yl)-1H,2H,3H-pyrazolo[3,4-d]pyrimidin-3-one (36.5 mg, 0.098 mmol, 1 equiv), toluene (2 mL, 0.022 mmol, 0.22 equiv), 1-(propan-2-yl)-1H-pyrazol-4-amine (14.68 mg, 0.117 mmol, 1.20 equiv), DIEA (37.90 mg, 0.293 mmol, 3 equiv). The resulting solution was stirred for 2 hr at room temperature. The resulting mixture was concentrated. The crude product (23 mg) was purified by Prep-HPLC with the following conditions: Column, X-bridge RP18; mobile phase, 0.05% FA in water and $CH_3CN$ (45% $CH_3CN$ up to 60% in 5 min); Detector, UV 254 nm. This resulted in 4.8 mg (10.43%) of 1-[6-(2-hydroxypropan-2-yl)pyridin-2-yl]-2-(prop-2-en-1-yl)-6-[[1-(propan-2-yl)-1H-pyrazol-4-yl]amino]-1H,2H,3H-pyrazolo[3,4-d]pyrimidin-3-one hydrochloride as a white solid. LC-MS (ES, m/z): 435[M+1]$^+$, $^1$H NMR (300 MHz, DMSO-d6, ppm) δ: 8.80 (s, 1H), 8.06-8.01 (m, 1H), 7.92 (s, 1H), 7.75 (d, J=8.1 Hz, 1H), 7.65 (d, J=7.5 Hz, 1H), 7.54 (s, 1H), 5.69-5.60 (m, 1H), 4.99 (d, J=10.2 Hz, 1H), 4.79 (d, J=17.1 Hz, 1H), 4.68-4.57 (m, 2H), 4.46-4.41 (m, 1H), 1.55-1.28 (m, 12H).

Example 7: Preparation of 6-[(1-cyclopentyl-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one Hydrochloride Synthesis of 1-cyclopentyl-4-nitro-1H-pyrazole: Into a 100-mL round-bottom flask, was placed 4-nitro-1H-pyrazole (1.13 g, 10 mmol, 1 equiv), DMF (20 mL). This was followed by the addition of NaH (0.8 g, 30 mmol, 3 equiv) at 0° C. for 30 min. To this was added bromocyclopentane (1.49 g, 10 mmol, 1 equiv) at 0° C. The resulting solution was stirred for overnight at 100° C. in an oil bath. The reaction mixture was cooled to room temperature with a water bath. The reaction was then quenched by the addition of 20 mL of water. The resulting solution was extracted with 3×30 mL of ethylacetate. The organic layer was dried over anhydrous sodium sulfate and concentrated under vacuum. This resulted in 1.0 g (55.20%) of 1-cyclopentyl-4-nitro-1H-pyrazole as yellow oil. LC-MS-1: (ES, m/z): 182[M+1]$^+$ Synthesis of 1-cyclopentyl-1H-pyrazol-4-amine: Into a 100-mL round-bottom flask, was placed 1-cyclopentyl-4-nitro-1H-pyrazole (1 g, 5.519 mmol, 1.0 equiv), MeOH (30 mL, 0.936 mmol, 0.17 equiv), Pd/C (200 mg, 1.879 mmol, 0.34 equiv), $H_2$. The resulting solution was stirred for overnight at room temperature. The solids were filtered out. The resulting mixture was concentrated and purified by Pre-TLC. This resulted in 200 mg (23.97%) of 1-cyclopentyl-1H-pyrazol-4-amine as a white solid. LC-MS-2: (ES, m/z): 152[M+1]$^+$ Synthesis of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (30 mg, 0.084 mmol, 1 equiv), toluene (2 mL, 0.022 mmol, 0.26 equiv), m-CPBA (14.48 mg, 0.084 mmol, 1.00 equiv). The resulting solution was stirred for 2 hr at room temperature. The resulting mixture was concentrated. This resulted in 31.3 mg (crude) of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one as a white solid. LC-MS-3: (ES, m/z): 374[M+1]$^+$ Synthesis of 6-[(1-cyclopentyl-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one hydrochloride: Into a 8-mL vial, was placed 1-[6-(2-hydroxypropan-2-yl)pyridin-2-yl]-6-methanesulfinyl-2-(prop-2-en-1-yl)-1H,2H,3H-pyrazolo[3,4-d]pyrimidin-3-one (31.34 mg, 0.084 mmol, 1 equiv), toluene (2 mL), DIEA (32.54 mg, 0.252 mmol, 3 equiv), 1-cyclopentyl-1H-pyrazol-4-amine (12.69 mg, 0.084 mmol, 1.00 equiv). The resulting solution was stirred for 2 hr at room temperature. The resulting mixture was concentrated. The crude product was purified by Prep-HPLC with the following conditions ( ): Column, X-bridge RP18; mobile phase, 0.05% FA in water and $CH_3CN$ (45% $CH_3CN$ up to 60% in 5 min); Detector, UV 254 nm. This resulted in 4.8 mg (11.51%) of 6-[(1-cyclopentyl-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one hydrochloride as a yellow solid. LC-MS-0: (ES, m/z): 461[M+1]$^+$, $^1$H NMR (300 MHz, DMSO-d6, ppm) δ 8.80 (s, 1H), 8.04-8.01 (m, 1H), 7.91 (s, 1H), 7.74 (d, J=8.1 Hz, 1H), 7.66 (d, J=7.5 Hz, 1H), 7.53 (d, J=0.6 Hz, 1H), 5.8-5.7 (m, 1H), 4.99 (d, J=9.9 Hz, 1H), 4.80 (d, J=17.4 Hz, 1H), 4.63 (d, J=6.3 Hz, 3H), 2.07 (s, 2H), 1.97-1.53 (m, 6H), 1.45 (s, 6H).

Example 8: Preparation of 6-[(1-cyclohexyl-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one Hydrochloride Synthesis of 1-cyclohexyl-4-nitro-1H-pyrazole: Into a 100-mL round-bottom flask, was placed 4-nitro-1H-pyrazole (1.13 g, 10 mmol, 1 equiv), DMF (20 mL). This was followed by the addition of NaH (0.8 g, 30 mmol, 3 equiv) at 0° C. for 30 min. To this was added bromocyclohexane (1.63 g, 10 mmol, 1 equiv) at 0° C. The resulting solution was stirred for overnight at 100 degrees C. in an oil bath. The reaction was then quenched by the addition of 20 mL of water. The resulting solution was extracted with 3×30 mL of ethyl acetate. The organic layer was dried over anhydrous sodium sulfate and concentrated under vacuum. This resulted in 400 mg (20.50%) of 1-cyclohexyl-4-nitro-1H-pyrazole as a white solid. LC-MS-1: (ES, m/z): 196[M+1]$^+$ Synthesis of 1-cyclohexyl-1H-pyrazol-4-amine: Into a 100-mL round-bottom flask, was placed 1-cyclohexyl-4-nitro-1H-pyrazole (400 mg, 2.049 mmol, 1 equiv), MeOH (20 mL), Pd/C (100 mg, 0.940 mmol, 0.46 equiv), H2. The resulting solution was stirred for overnight at room temperature. The solids were filtered out. The resulting mixture was concentrated and purified by Pre-TLC. This resulted in 98 mg (28.95%) of 1-cyclohexyl-1H-pyrazol-4-amine as a white solid. LC-MS-2: (ES, m/z): 166[M+1]$^+$ Synthesis of 1-[6-(2-hydroxypropan-2-yl) pyridin-2-yl]-6-methanesulfinyl-2-(prop-2-en-1-yl)-1H, 2H, 3H-pyrazolo[3, 4-d] pyrimidin-3-one: Into a 8-mL vial, was placed 1-[6-(2-hydroxypropan-2-yl)pyridin-2-yl]-6-(methylsulfanyl)-2-(prop-2-en-1-yl)-1H,2H,3H-pyrazolo[3,4-d]pyrimidin-3-one (30 mg, 0.084 mmol, 1 equiv), toluene (2 mL), m-CPBA (14.48 mg, 0.084 mmol, 1.00 equiv). The resulting solution was stirred for 2 hr at room temperature. The resulting mixture was concentrated. This resulted in 31.3 mg (crude) of 1-[6-(2-hydroxypropan-2-yl) pyridin-2-yl]-6-methanesulfinyl-2-(prop-2-en-1-yl)-1H, 2H, 3H-pyrazolo [3, 4-d] pyrimidin-3-one as a white solid. LC-MS-3: (ES, m/z): 374[M+1]$^+$ Synthesis of 6-[(1-cyclohexyl-1H-pyrazol-4-yl)amino]-1-[6-(2-hydroxypropan-2-yl)pyridin-2-yl]-2-(prop-2-en-1-yl)-1H,2H,3H-pyrazolo[3,4-d]pyrimidin-3-one hydrochloride: Into a 8-mL vial, was placed 1-[6-(2-hydroxypropan-2-yl) pyridin-2-yl]-6-methanesulfinyl-2-(prop-2-en-1-yl)-1H,2H, 3H-pyrazolo[3,4-d]pyrimidin-3-one (31.34 mg, 0.084 mmol, 1 equiv), toluene (2 mL), 1-cyclohexyl-1H-pyrazol-4-amine (13.87 mg, 0.084 mmol, 1.00 equiv), DIEA (32.54 mg, 0.252 mmol, 3 equiv). The resulting solution was stirred for 2 hr at room temperature. The resulting mixture was concentrated. The crude product was purified by Prep-HPLC with the following conditions: Column, X-bridge RP18; mobile phase, 0.05% FA in water and CH$_3$CN (45% CH$_3$CN up to 60% in 5 min); Detector, UV 254 nm. This resulted in 4.5 mg (10.49%) of 6-[(1-cyclohexyl-1H-pyrazol-4-yl) amino]-1-[6-(2-hydroxypropan-2-yl)pyridin-2-yl]-2-(prop-2-en-1-yl)-1H,2H,3H-pyrazolo[3,4-d]pyrimidin-3-one hydrochloride as a white solid. LC-MS (ES, m/z): 475[M+1]$^+$ $^1$H NMR (300 MHz, DMSO-d$_6$, ppm) δ 8.79 (s, 1H), 8.06-7.89 (m, 2H), 7.75-7.73 (m, 2H), 7.52 (s, 1H), 5.63-5.61 (m, 1H), 4.99 (d, J=10.2 Hz, 1H), 4.80 (d, J=17.4 Hz, 1H), 4.62 (d, J=6.0 Hz, 2H), 1.98 (s, 2H), 1.81 (s, 2H), 1.66 (s, 3H), 1.45 (s, 10H).

Example 9: Preparation of 1-[6-(2-hydroxypropan-2-yl)pyridin-2-yl]-6-[[4-(4-methylpiperazin-1-yl)phenyl]amino]-2-(propan-2-yl)-1H,2H,3H-pyrazolo[3,4-d]pyrimidin-3-one Synthesis of ethyl 4-hydrazinyl-2-(methylsulfanyl)pyrimidine-5-carboxylate: Into a 1000-mL 3-necked round-bottom flask, was placed a solution of ethyl 4-chloro-2-(methylsulfanyl)pyrimidine-5-carboxylate (30 g, 128.932 mmol, 1 equiv) in EtOH (300 mL). This was followed by the addition of a solution of NH$_2$NH$_2$H$_2$O (19.36 g, 386.733 mmol, 3.00 equiv) in EtOH (300 mL) dropwise with stirring at 0 degree. The resulting solution was stirred for 1 hr at 0 degree. The solids were collected by filtration. This resulted in 20 g (67.95%) of ethyl 4-hydrazinyl-2-(methylsulfanyl) pyrimidine-5-carboxylate as a white solid. $^1$H-NMR (300 MHz, CD$_3$OD, ppm): δ 8.53 (s, 1H), 4.39-4.32 (m, 2H), 2.60 (s, 3H), 4.40-1.35 (m, 3H).

Synthesis of ethyl 2-(methylsulfanyl)-4-[2-(propan-2-ylidene)hydrazin-1-yl]pyrimidine-5-carboxylate: Into a 1000-mL round-bottom flask, was placed ethyl 4-hydrazinyl-2-(methylsulfanyl)pyrimidine-5-carboxylate (20 g, 87.616 mmol, 1 equiv), propan-2-one (600 mL). The resulting solution was stirred for 12 hr at 70 degree. The resulting mixture was concentrated. This resulted in 20 g (85.07%) of ethyl 2-(methylsulfanyl)-4-[2-(propan-2-ylidene)hydrazin-1-yl]pyrimidine-5-carboxylate as a white solid. $^1$H-NMR-2 (300 MHz, CDCl$_3$, ppm): δ 8.75 (s, 1H), 4.40-4.33 (m, 2H), 2.61-2.58 (m, 3H), 2.18-2.16 (m, 3H), 2.04 (s, 3H), 1.42-1.38 (m, 3H).

Synthesis of ethyl 2-(methylsulfanyl)-4-[2-(propan-2-yl)hydrazin-1-yl]pyrimidine-5-carboxylate: Into a 1000-mL 4-necked round-bottom flask, was placed ethyl 2-(methylsulfanyl)-4-[2-(propan-2-ylidene)hydrazin-1-yl]pyrimidine-5-carboxylate (20 g, 74.532 mmol, 1 equiv), MeOH (500 mL). This was followed by the addition of NaBH$_3$CN (23.42 g, 372.681 mmol, 5.00 equiv), in portions at 0° C. The resulting solution was stirred for 1 overnight at room temperature. The reaction was then quenched by the addition of 1000 mL of water. The organic layer was extracted with 2×1000 mL of ethyl acetate The organic layer was washed with 2×1000 ml of Brine. The mixture was dried over anhydrous sodium sulfate and concentrated. This resulted in 20 g (99.26%) of ethyl 2-(methylsulfanyl)-4-[2-(propan-2-yl)hydrazin-1-yl]pyrimidine-5-carboxylate as a white solid. $^1$H-NMR-3: (300 MHz, CDCl$_3$, ppm): δ 8.65-8.63 (m, 1H), 4.42-4.32 (m, 3H), 3.28-3.20 (m, 1H), 2.50 (s, 3H), 2.11 (s, 3H), 1.45-1.39 (m, 3H), 1.33-1.28 (m, 6H).

Synthesis of 6-(methylsulfanyl)-2-(propan-2-yl)-1H,2H,3H-pyrazolo[3,4-d]pyrimidin-3-one: Into a 500-mL round-bottom flask, was placed ethyl 2-(methylsulfanyl)-4-[2-(propan-2-yl)hydrazin-1-yl]pyrimidine-5-carboxylate (20 g, 73.978 mmol, 1 equiv), EtOH (200 mL). This was followed by the addition of NaOH (14.79 g, 6M, 62 ml, 369.777 mmol, 5.00 equiv) dropwise with stirring at 0 degree. The resulting solution was stirred for 2 hr at room temperature. The resulting mixture was concentrated. The residue was applied onto a silica gel column with dichloromethane/methanol (1:0-10:1). This resulted in 15 g (70%) of 6-(methylsulfanyl)-2-(propan-2-yl)-1H,2H,3H-pyrazolo[3,4-d]pyrimidin-3-one as a yellow solid. $^1$H-NMR-4 $^1$H-NMR (300 MHz, DMSO-d6, ppm): δ 8.16 (s, 1H), 4.62-4.53 (m, 1H), 2.45-2.42 (m, 3H), 1.26-1.10 (m, 6H).

Synthesis of 1-[6-(2-hydroxypropan-2-yl)pyridin-2-yl]-6-(methylsulfanyl)-2-(propan-2-yl)-1H,2H,3H-pyrazolo[3,4-d]pyrimidin-3-one: Into a 100-mL round-bottom flask, was placed 2-(6-bromopyridin-2-yl)propan-2-ol (5.78 g, 26.750 mmol, 3.00 equiv), 6-(methylsulfanyl)-2-(propan-2-yl)-1H, 2H,3H-pyrazolo[3,4-d]pyrimidin-3-one (2 g, 8.917 mmol, 1 equiv), methyl[2-(methylamino)ethyl]amine (0.79 g, 8.917 mmol, 1 equiv), CuI (1.70 g, 8.917 mmol, 1 equiv), K$_2$CO$_3$ (3.70 g, 26.752 mmol, 3 equiv), Dioxane (30 mL). The resulting solution was stirred for 12 hr at 95° C. The solids were filtered out. The resulting mixture was concentrated. The residue was applied onto a silica gel column with ethyl acetate/petroleum ether (0:1-2:1). This resulted in 1 g (31.20%) of 1-[6-(2-hydroxypropan-2-yl)pyridin-2-yl]-6-

(methylsulfanyl)-2-(propan-2-yl)-1H,2H,3H-pyrazolo[3,4-d]pyrimidin-3-one as a white solid. LC-MS-5: [M+1]=360, $^1$H-NMR-5: (300 MHz, CDCl$_3$, ppm): δ 8.89 (s, 1H), 7.96-7.91 (m, 1H), 7.72-7.70 (m, 1H), 7.74-7.42 (m, 1H), 4.35-4.30 (m, 1H), 2.57 (s, 3H), 1.64 (s, 6H), 1.54-1.52 (m, 6H).

Synthesis of 1-[6-(2-hydroxypropan-2-yl)pyridin-2-yl]-6-methanesulfinyl-2-(propan-2-yl)-1H,2H,3H-pyrazolo[3,4-d]pyrimidin-3-one: Into a 8-mL vial, was placed 1-[6-(2-hydroxypropan-2-yl)pyridin-2-yl]-6-(methylsulfanyl)-2-(propan-2-yl)-1H,2H,3H-pyrazolo[3,4-d]pyrimidin-3-one (100 mg, 0.278 mmol, 1 equiv), toluene (3 mL), m-CPBA (48.01 mg, 0.278 mmol, 1 equiv). The resulting solution was stirred for 2 hr at room temperature. The resulting mixture was concentrated. This resulted in 104 mg (99.57%) of 1-[6-(2-hydroxypropan-2-yl)pyridin-2-yl]-6-methanesulfinyl-2-(propan-2-yl)-1H,2H,3H-pyrazolo [3,4-d]pyrimidin-3-one as a white solid. LC-MS-10: (ES, m/z): 376[M+1]$^+$ Synthesis of 1-[6-(2-hydroxypropan-2-yl)pyridin-2-yl]-6-[[4-(4-methylpiperazin-1-yl)phenyl]amino]-2-(propan-2-yl)-1H,2H,3H-pyrazolo[3,4-d]pyrimidin-3-one: Into a 8-mL vial, was placed 1-[6-(2-hydroxypropan-2-yl)pyridin-2-yl]-6-methanesulfinyl-2-(propan-2-yl)-1H,2H,3H-pyrazolo[3,4-d]pyrimidin-3-one (104 mg, 0.277 mmol, 1 equiv), toluene (5 mL), 4-(4-methylpiperazin-1-yl)aniline (52.98 mg, 0.277 mmol, 1.00 equiv), DIEA (107.40 mg, 0.831 mmol, 3 equiv). The resulting solution was stirred for 2 hr at room temperature. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector, UV 254 nm. This resulted in 11.1 mg (7.97%) of 1-[6-(2-hydroxypropan-2-yl)pyridin-2-yl]-6-[[4-(4-methylpiperazin-1-yl)phenyl]amino]-2-(propan-2-yl)-1H,2H,3H-pyrazolo[3,4-d]pyrimidin-3-one as a light yellow solid. LC-MS-10 (ES, m/z): 503[M+1], $^1$H NMR (300 MHz, DMSO-d6, ppm) δ 10.06 (s, 1H), 8.75 (s, 1H), 8.06 (d, J=8.1 Hz, 1H), 7.75-7.62 (m, 2H), 7.55 (d, J=8.4 Hz, 2H), 6.90 (d, J=9.0 Hz, 2H), 5.31 (s, 1H), 4.24-4.09 (m, 1H), 3.15-3.04 (m, 4H), 2.46-2.45 (m, 4H), 2.23 (s, 3H), 1.45 (s, 6H), 1.37 (d, J=6.9 Hz, 6H).

Example 10: Preparation of 6-[[4-(4-methylpiperazin-1-yl)phenyl]amino]-2-(propan-2-yl)-1-[6-(trifluoromethyl)pyridin-2-yl]-1H,2H,3H-pyrazolo[3,4-d]pyrimidin-3-one Synthesis of 6-(methylsulfanyl)-2-(propan-2-yl)-1-[6-(trifluoromethyl)pyridin-2-yl]-1H,2H,3H-pyrazolo[3,4-d]pyrimidin-3-one: Into a 100-mL round-bottom flask, was placed 2-bromo-6-(trifluoromethyl)pyridine (4.51 g, 19.956 mmol, 2.00 equiv), 6-(methylsulfanyl)-2-(propan-2-yl)-1H,2H,3H-pyrazolo[3,4-d]pyrimidin-3-one (2.24 g, 9.988 mmol, 1 equiv), methyl[2-(methylamino)ethyl]amine (0.88 g, 9.988 mmol, 1 equiv), CuI (1.90 g, 9.988 mmol, 1 equiv), K$_2$CO$_3$ (4.14 g, 29.963 mmol, 3 equiv), Dioxane (50 mL). The resulting solution was stirred for overnight at 95° C. The resulting mixture was concentrated. The residue was applied onto a silica gel column with ethyl acetate/petroleum ether (0:1-1:2). This resulted in 1 g (27.11%) of 6-(methylsulfanyl)-2-(propan-2-yl)-1-[6-(trifluoromethyl)pyridin-2-yl]-1H,2H,3H-pyrazolo[3,4-d]pyrimidin-3-one as a yellow solid. $^1$H-NMR-5: (300 MHz, CDCl$_3$, 300 ppm): δ 8.92 (s, 1H), 8.22-8.19 (m, 1H), 8.09-8.07 (m, 1H), 7.66-7.64 (dd, J=6 Hz, 1H), 4.34-4.25 (m, 1H), 2.61 (s, 1H), 1.61-1.57 (s, 6H).

Synthesis of 6-methanesulfinyl-2-(propan-2-yl)-1-[6-(trifluoromethyl)pyridin-2-yl]-1H,2H,3H-pyrazolo[3,4-d]pyrimidin-3-one: Into a 8-mL vial, was placed 6-(methylsulfanyl)-2-(propan-2-yl)-1-[6-(trifluoromethyl)pyridin-2-yl]-1H,2H,3H-pyrazolo[3,4-d]pyrimidin-3-one (100 mg, 0.271 mmol, 1 equiv), toluene (3 mL), m-CPBA (46.72 mg, 0.271 mmol, 1 equiv). The resulting solution was stirred for 2 hr at room temperature. The resulting mixture was concentrated. This resulted in 104 mg (crude) of 6-methanesulfinyl-2-(propan-2-yl)-1-[6-(trifluoromethyl)pyridin-2-yl]-1H,2H,3H-pyrazolo[3,4-d]pyrimidin-3-one as a white solid. LC-MS-10: (ES, m/z): 386[M+1]$^+$ Synthesis of 6-[[4-(4-methylpiperazin-1-yl)phenyl]amino]-2-(propan-2-yl)-1-[6-(trifluoromethyl)pyridin-2-yl]-1H,2H,3H-pyrazolo[3,4-d]pyrimidin-3-one: Into a 8-mL vial, was placed 6-methanesulfinyl-2-(propan-2-yl)-1-[6-(trifluoromethyl)pyridin-2-yl]-1H,2H,3H-pyrazolo[3,4-d]pyrimidin-3-one (104 mg, 0.270 mmol, 1 equiv), toluene (4 mL), 4-(4-methylpiperazin-1-yl)aniline (51.62 mg, 0.270 mmol, 1.00 equiv), DIEA (104.64 mg, 0.810 mmol, 3 equiv). The resulting solution was stirred for 3 hr at room temperature. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector, UV 254 nm. This resulted in 13.7 mg (9.90%) of 6-[[4-(4-methylpiperazin-1-yl)phenyl]amino]-2-(propan-2-yl)-1-[6-(trifluoromethyl)pyridin-2-yl]-1H,2H,3H-pyrazolo[3,4-d]pyrimidin-3-one as a light yellow solid. LC-MS-0: (ES, m/z): 513[M+1], $^1$H NMR (300 MHz, DMSO-d6, ppm): δ 10.21 (s, 1H), 8.80 (s, 1H), 8.37 (d, J=7.8 Hz, 1H), 8.22 (s, 1H), 7.89 (d, J=7.5 Hz, 1H), 7.55 (d, J=8.7 Hz, 2H), 6.93 (d, J=8.7 Hz, 2H), 4.21-4.05 (m, 1H), 3.12-3.09 (m, 4H), 2.49-2.47 (m, 4H), 2.23 (s, 3H), 1.37 (d, J=6.9 Hz, 6H).

Example 11: Preparation of 2-isopropyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one Synthesis of 2-bromo-6-[1,1,1-trifluoro-2-[(trimethylsilyl)oxy]propan-2-yl]pyridine: Into a 250-mL 3-necked round-bottom flask, was placed 1-(6-bromopyridin-2-yl)ethan-1-one (20 g, 99.983 mmol, 1 equiv), KOAc (9.8 g, 99.983 mmol, 1 equiv), DMSO (150 mL). This was followed by the addition of a solution of trimethyl(trifluoromethyl)silane (31.28 g, 219.962 mmol, 2.2 equiv) in DMSO (50 mL) dropwise with stirring at 25° C. The resulting solution was stirred for overnight at room temperature. The reaction was then quenched by the addition of 300 mL of water. The resulting solution was extracted with 3×100 mL of ethyl acetate. The organic layer was washed with 3×100 ml of Brine. The mixture was dried over anhydrous sodium sulfate and concentrated. This resulted in 34.2 g (crude) of 2-bromo-6-[1,1,1-trifluoro-2-[(trimethylsilyl)oxy]propan-2-yl]pyridine as purple oil. LC-MS-1 (ES, m/z): M+1=344

Synthesis of 2-(6-bromopyridin-2-yl)-1,1,1-trifluoropropan-2-ol: Into a 500-mL round-bottom flask, was placed 2-bromo-6-[1,1,1-trifluoro-2-[(trimethylsilyl)oxy]propan-2-yl]pyridine (34.2 g, 99.933 mmol, 1 equiv), K$_2$CO$_3$ (27.82 g, 199.865 mmol, 2 equiv), MeOH (200 mL). The resulting solution was stirred for 1 hr at room temperature. The solids were filtered out. The resulting mixture was concentrated. The resulting solution was extracted with 2×100 mL of ethyl acetate. The organic layer was washed with 2×100 ml of Brine. The mixture was dried over anhydrous sodium sulfate and concentrated. This resulted in 27 g (crude) of 2-(6-bromopyridin-2-yl)-1,1,1-trifluoropropan-2-ol as a purple solid. $^1$H-NMR-2 (300 MHz, CDCl$_3$, ppm): δ 7.71-7.66 (m, 1H), 7.59-7.56 (m, 1H), 7.51-7.48 (m, 1H), 7.55 (s, 1H), 1.79 (s, 3H).

Synthesis of 2-(6-bromopyridin-2-yl)-1,1,1-trifluoropropan-2-yl methanesulfonate: Into a 500-mL round-bottom flask, was placed 2-(6-bromopyridin-2-yl)-1,1,1-trifluoropropan-2-ol (27 g, 99.982 mmol, 1 equiv), THF (270 mL). This was followed by the addition of NaH (8 g, 0.2 mmol, 2.0 equiv, 60%), in portions at 40° C. The resulting solution was stirred for 0.5 hr at 40° C. To this was added a solution of MsCl (22.91 g, 199.964 mmol, 2.0 equiv) in THF (70 mL) dropwise with stirring at 40° C. The resulting solution was stirred for overnight at room temperature. The reaction was then quenched by the addition of 200 mL of water/ice. The resulting solution was extracted with 2×100 mL of ethyl acetate. The organic layer was washed with 2×100 ml of Brine. The mixture was dried over anhydrous sodium sulfate and concentrated. The residue was applied onto a silica gel column and eluted with ethyl acetate/petroleum ether (0:1-1:5). This resulted in 28 g (80.44%) of 2-(6-bromopyridin-2-yl)-1,1,1-trifluoropropan-2-yl methanesulfonate as purple oil. $^1$H-NMR-3 (300 MHz, CDCl$_3$, ppm): δ 7.70-7.64 (m, 2H), 7.59-7.54 (m, 1H), 3.27 (s, 3H), 2.31 (s, 3H).

Synthesis of 2-bromo-6-(1,1,1-trifluoro-2-methylpropan-2-yl)pyridine: Into a 100-mL round-bottom flask, was placed 2-(6-bromopyridin-2-yl)-1,1,1-trifluoropropan-2-yl methanesulfonate (3.5 g, 10.054 mmol, 1 equiv), DCM (30 mL, 471.901 mmol, 46.94 equiv). This was followed by the addition of trimethylalumane/Hexane (20 mL, 20 mmol, 2.0 equiv) dropwise with stirring at 25° C. The resulting solution was stirred for overnight at room temperature. The reaction was then quenched by the addition of 100 mL of water/ice. The resulting solution was extracted with 2×100 mL of chloromethane. The organic layer was washed with 3×100 of Brine. The mixture was dried over anhydrous sodium sulfate and concentrated. The crude product was purified by Flash-Prep-HPLC with the following conditions (IntelFlash-1): Column, C18 silica gel; mobile phase, Water (0.1% FA) and ACN (48.0% ACN up to 53.0% in 7 min, hold 95.0% in 1 min, down to 48.0% in 1 min within 5; Detector, UV 254 nm. This resulted in 120 mg (4.45%) of 2-bromo-6-(1,1,1-trifluoro-2-methylpropan-2-yl)pyridine as colorless oil. $^1$H-NMR-4 (300 MHz, CDCl$_3$, ppm): δ 7.58-7.41 (m, 3H), 1.61-1.58 (m, 6H).

Synthesis of 6-(methylsulfanyl)-2-(propan-2-yl)-1-[6-(1,1,1-trifluoro-2-methylpropan-2-yl)pyridin-2-yl]-1H,2H,3H-pyrazolo[3,4-d]pyrimidin-3-one: Into a 8-mL round-bottom flask, was placed 6-(methylsulfanyl)-2-(propan-2-yl)-1H,2H,3H-pyrazolo[3,4-d]pyrimidin-3-one (112 mg, 0.499 mmol, 1 equiv), 2-bromo-6-(1,1,1-trifluoro-2-methylpropan-2-yl)pyridine (133.87 mg, 0.499 mmol, 1.00 equiv), methyl[2-(methylamino)ethyl]amine (44.02 mg, 0.499 mmol, 1 equiv), CuI (95.11 mg, 0.499 mmol, 1 equiv), K$_2$CO$_3$ (207.05 mg, 1.498 mmol, 3 equiv), Dioxane (5 mL). The resulting solution was stirred for overnight at 95° C. The resulting mixture was concentrated. The residue was applied onto a silica gel column and eluted with ethyl acetate/petroleum ether (0:1-1:3). This resulted in 100 mg (48.67%) of 6-(methylsulfanyl)-2-(propan-2-yl)-1-[6-(1,1,1-trifluoro-2-methylpropan-2-yl)pyridin-2-yl]-1H,2H,3H-pyrazolo[3,4-d]pyrimidin-3-one as a white solid. LC-MS-5 (ES, m/z): M+1=412, $^1$H-NMR-5 (300 MHz, CDCl$_3$, ppm): δ 8.90 (s, 1H), 7.96-7.90 (m, 1H), 7.85-7.82 (m, 1H), 7.51-7.49 (m, 1H), 4.36-4.26 (m, 1H), 2.58 (s, 3H), 1.64 (s, 6H), 1.57-1.54 (m, 6H).

Synthesis of 6-methanesulfinyl-2-(propan-2-yl)-1-[6-(1,1,1-trifluoro-2-methylpropan-2-yl)pyridin-2-yl]-1H,2H,3H-pyrazolo[3,4-d]pyrimidin-3-one: Into a 8-mL vial, was placed 6-(methylsulfanyl)-2-(propan-2-yl)-1-[6-(1,1,1-trifluoro-2-methylpropan-2-yl)pyridin-2-yl]-1H,2H,3H-pyrazolo[3,4-d]pyrimidin-3-one (50 mg, 0.122 mmol, 1 equiv), toluene (4 mL), m-CPBA (20.97 mg, 0.122 mmol, 1.00 equiv). The resulting solution was stirred for 3 hr at room temperature. The resulting mixture was concentrated. This resulted in 51.8 mg (crude) of 6-methanesulfinyl-2-(propan-2-yl)-1-[6-(1,1,1-trifluoro-2-methylpropan-2-yl)pyridin-2-yl]-1H,2H,3H-pyrazolo[3,4-d]pyrimidin-3-one as a white solid. LC-MS-6 (ES, m/z): 428[M+1]$^+$ Synthesis of 2-isopropyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one: Into a 8-mL vial, was placed 6-methanesulfinyl-2-(propan-2-yl)-1-[6-(1,1,1-trifluoro-2-methylpropan-2-yl)pyridin-2-yl]-1H,2H,3H-pyrazolo[3,4-d]pyrimidin-3-one (51.8 mg, 0.121 mmol, 1 equiv), 4-(4-methylpiperazin-1-yl)aniline (23.18 mg, 0.121 mmol, 1.00 equiv), toluene (5 mL), DIEA (46.99 mg, 0.364 mmol, 3 equiv). The resulting solution was stirred for 3 hr at room temperature. The resulting mixture was concentrated. The crude product was purified by Prep-HPLC with the following conditions: Column, X-bridge RP18; mobile phase, 0.05% ammonia in water and CH$_3$CN (45% CH$_3$CN up to 60% in 5 min); Detector, UV 254 nm. This resulted in 8 mg (11.90%) of 2-isopropyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one as a yellow solid. LC-MS-0 (ES, m/z): 555[M+1]$^+$, $^1$H-NMR (300 MHz, DMSO-d$_6$, ppm): δ 10.12 (s, 1H), 8.76 (s, 1H), 8.15 (d, J=8.1 Hz, 1H), 7.90 (d, J=8.1 Hz, 1H), 7.64 (d, J=7.8 Hz, 1H), 7.55 (d, J=8.4 Hz, 2H), 6.91 (d, J=9.0 Hz, 2H), 4.19-4.10 (m, 1H), 3.17-3.02 (m, 4H), 2.49-2.46 (m, 4H), 2.23 (s, 3H), 1.61 (s, 6H), 1.37 (d, J=6.9 Hz, 6H).

Example 12: Preparation of 2-cyclopropyl-6-[[4-(4-methylpiperazin-1-yl)phenyl]amino]-1-[6-(1,1,1-trifluoro-2-methylpropan-2-yl)pyridin-2-yl]-1H,2H,3H-pyrazolo[3,4-d]pyrimidin-3-one Synthesis of N-cyclopropyl-N-oxo(tert-butoxy)carbohydrazide: Into a 250-mL 3-necked round-bottom flask, was placed tert-butyl N-cyclopropylcarbamate (4.80 g, 30.532 mmol, 1.0 equiv), ACN (100.00 mL, 1902.470 mmol, 62.31 equiv), Py (4.83 g, 61.14 mmol, 2.0 equiv). This was followed by the addition of Nitrosonium tetrafluoroborate (4.70 g, 30.532 mmol, 1.0 equiv), in portions at 0 degrees C. The resulting solution was stirred for overnight at room temperature. The reaction was then quenched by the addition of 100 mL of water. The resulting solution was extracted with 2×100 mL of ethyl acetate. The resulting mixture was washed with 2×100 ml of Brine. The mixture was dried over anhydrous sodium sulfate and concentrated. The residue was applied onto a silica gel column and eluted with ethyl acetate/petroleum ether (0:1-1:10). This resulted in 1.5 g (26.38%) of N-cyclopropyl-N-oxo(tert-butoxy)carbohydrazide as yellow oil. LC-MS-1 (ES, m/z): M+1=187. $^1$H-NMR-1 (300 MHz, CDCl$_3$, 300 ppm): δ 2.36-2.31 (m, 1H), 1.65 (s, 9H), 1.10-1.03 (m, 2H), 0.61-0.51 (m, 2H).

Synthesis of N-cyclopropyl(tert-butoxy)carbohydrazide: Into a 40-mL round-bottom flask, was placed N-cyclopropyl-N-oxo(tert-butoxy)carbohydrazide (1.50 g, 8.055 mmol, 1.00 equiv), EtOH (10.00 mL), H$_2$O (10.00 mL), NH$_4$Cl (4.31 g, 80.554 mmol, 10.00 equiv). This was followed by the addition of Zn (5.27 g, 80.554 mmol, 10.00 equiv), in portions at 0 degrees C. The resulting solution was stirred for overnight at room temperature. The solids were filtered out. The resulting solution was extracted with 2×20 mL of ethyl acetate concentrated. The residue was applied onto a silica gel column and eluted with ethyl acetate/petroleum ether (0:1-1:0). This resulted in 300 mg (21.62%) of N-cyclopropyl(tert-butoxy)carbohydrazide as a white oil. H-NMR-2 (300 MHz, CDCl$_3$, 300 ppm): δ 2.83-2.78 (m, 1H), 1.37 (s, 9H), 0.66-0.59 (m, 4H).

Synthesis of ethyl 4-([N-cyclopropyl[(tert-butoxy)carbonyl] amino]amino)-2-(methylsulfanyl)pyrimidine-5-carboxylate: Into a 8-mL round-bottom flask, was placed N-cyclopropyl(tert-butoxy)carbohydrazide (222.06 mg, 1.289 mmol, 1 equiv), ethyl 4-chloro-2-(methylsulfanyl)pyrimidine-5-carboxylate (300.00 mg, 1.289 mmol, 1.00 equiv), THF (5.00 mL), DIEA (416.59 mg, 3.22 mmol, 2.5 equiv). The resulting solution was stirred for overnight at 70 degrees C. The resulting mixture was concentrated. The residue was applied onto a silica gel column and eluted with ethyl acetate/petroleum ether (0:1-1:1). This resulted in 200 mg (42.10%) of ethyl 4-([N-cyclopropyl[(tert-butoxy)carbonyl]amino]amino)-2-(methylsulfanyl)pyrimidine-5-carboxylate as a white solid. LC-MS-3 (ES, m/z): M+1=369.

Synthesis of 4-(2-cyclopropylhydrazin-1-yl)-2-(methylsulfanyl) pyrimidine-5-carboxylate: Into a 8-mL round-bottom flask, was placed ethyl 4-([N-cyclopropyl[(tert-butoxy)carbonyl]amino] amino)-2-(methylsulfanyl)pyrimidine-5-carboxylate (200.00 mg, 0.543 mmol, 1.00 equiv), DCM (3 mL), TFA (618.93 mg, 5.428 mmol, 10.00 equiv). The resulting solution was stirred for overnight at room temperature. The resulting mixture was concentrated. This resulted in 160 mg (109.85%) of ethyl 4-(2-cyclopropylhydrazin-1-yl)-2-(methylsulfanyl) pyrimidine-5-carboxylate as a yellow crude solid. LC-MS-4 (ES, m/z): M+1=255

Synthesis of 2-cyclopropyl-6-(methylsulfanyl)-1H,2H,3H-pyrazolo[3,4-d]pyrimidin-3-one: Into a 8-mL round-bottom flask, was placed ethyl 4-(2-cyclopropylhydrazin-1-yl)-2-(methylsulfanyl) pyrimidine-5-carboxylate (160.00 mg, 0.596 mmol, 1.00 equiv), EtOH (2 mL). This was followed by the addition of a solution of NaOH (143.09 mg, 3.578 mmol, 6.00 equiv) in H$_2$O (1 mL) dropwise with stirring at 0 degrees C. The resulting solution was stirred for 1 h at room temperature. The pH value of the solution was adjusted to 7 with HCl (1 mol/L). The resulting mixture was concentrated. The residue was applied onto a silica gel column and eluted with dichloromethane/methanol (1:0-10:1). This resulted in 100 mg (75.45%) of 2-cyclopropyl-6-(methylsulfanyl)-1H,2H,3H-pyrazolo[3,4-d]pyrimidin-3-one as a yellow solid. $^1$H-NMR-5 (300 MHz, d-DMSO, 300 ppm): δ 8.73-8.64 (m, 1H), 3.51-3.17 (m, 4H), 1.24-1.16 (m, 1H), 1.08-0.83 (m, 4H).

Synthesis of 2-cyclopropyl-6-(methylsulfanyl)-1-[6-(1,1,1-trifluoro-2-methylpropan-2-yl)pyridin-2-yl]-1H,2H,3H-pyrazolo[3,4-d]pyrimidin-3-one: Into a 8-mL round-bottom flask, was placed 2-cyclopropyl-6-(methylsulfanyl)-1H,2H,3H-pyrazolo [3,4-d]pyrimidin-3-one (111.00 mg, 0.499 mmol, 1.00 equiv), 2-bromo-6-(1,1,1-trifluoro-2-methylpropan-2-yl)pyridine (133.88 mg, 0.499 mmol, 1.00 equiv), CuI (95.11 mg, 0.499 mmol, 1.00 equiv), K$_2$CO$_3$ (207.06 mg, 1.498 mmol, 3.00 equiv), dioxane (5 mL), N1,N2-dimethylethane-1,2-diamine (43.95 mg, 0.499 mmol, 1.00 equiv). The resulting solution was stirred for overnight at 95 degrees C. The resulting mixture was concentrated. The residue was applied onto a silica gel column and eluted with ethyl acetate/petroleum ether (0:1-1:3). This resulted in 60 mg (29.34%) of 2-cyclopropyl-6-(methylsulfanyl)-1-[6-(1,1,1-trifluoro-2-methylpropan-2-yl)pyridin-2-yl]-1H,2H,3H-pyrazolo[3,4-d]pyrimidin-3-one as a yellow solid. LC-MS-6 (ES, m/z): M+1=410

Synthesis of 2-cyclopropyl-6-[[4-(4-methylpiperazin-1-yl)phenyl]amino]-1-[6-(1,1,1-trifluoro-2-methylpropan-2-yl)pyridin-2-yl]-1H,2H,3H-pyrazolo[3,4-d]pyrimidin-3-one: Into a 40-mL vial, was placed 2-cyclopropyl-6-(methylsulfanyl)-1-[6-(1,1,1-trifluoro-2-methylpropan-2-yl)pyridin-2-yl]-1H,2H,3H-pyrazolo[3,4-d]pyrimidin-3-one (69.00 mg, 0.169 mmol, 1.00 equiv), toluene, m-CPBA (31.99 mg, 0.185 mmol, 1.10 equiv). The resulting solution was stirred for 3 h at room temperature. 4-(4-methylpiperazin-1-yl) aniline (35.46 mg, 0.185 mmol, 1.10 equiv), DIEA (65.34 mg, 0.506 mmol, 3.00 equiv). The resulting solution was stirred for overnight at room temperature. The resulting mixture was concentrated under vacuum. The residue was applied onto a silica gel column and eluted with dichloromethane/methanol (10:1). The collected fractions were combined and concentrated. This resulted in 19 mg of 2-cyclopropyl-6-[[4-(4-methylpiperazin-1-yl)phenyl]amino]-1-[6-(1,1,1-trifluoro-2-methylpropan-2-yl)pyridin-2-yl]-1H,2H,3H-pyrazolo[3,4-d]pyrimidin-3-one as a yellow solid. LC-MS-0 (ES, m/z): 553[M+1], $^1$H-NMR-0: 1H NMR (300 MHz, DMSO-d6, ppm): δ 10.04 (s, 1H), 8.75 (s, 1H), 8.17 (t, J=8.1 Hz, 1H), 7.90 (d, J=8.1 Hz, 1H), 7.61-7.59 (m, 3H), 6.92 (d, J=9.0 Hz, 2H), 3.21 (s, 1H), 3.16-3.06 (m, 4H), 2.46 (t, J=5.1 Hz, 4H), 2.23 (s, 3H), 1.61 (s, 6H), 0.87-0.75 (m, 4H).

Example 13: Preparation of 1-(6-(2-fluoropropan-2-yl)pyridin-2-yl)-2-isopropyl-6-((4-(4-methylpiperazin-1-yl)phenyl)amino)-1,2-dihydro-3H-pyrazolo[3,4-d]pyrimidin-3-one Synthesis of 2-bromo-6-(2-fluoropropan-2-yl)pyridine: Into a 100-mL 3-necked round-bottom flask purged and maintained with an inert atmosphere of nitrogen, was placed 2-(6-bromopyridin-2-yl)propan-2-ol (500.00 mg, 2.314 mmol, 1.00 equiv), DCM (20.00 mL). This was followed by the addition of DAST (1118.96 mg, 6.942 mmol, 3.00 equiv) dropwise with stirring at −78 degrees C. The resulting solution was stirred for overnight at room temperature. The reaction was then quenched by the addition of 20 mL of NaHCO$_3$ (5 mol/L). The resulting solution was extracted with 3×20 mL of dichloromethane concentrated under vacuum. The residue was applied onto a silica gel column and eluted with ethyl acetate/petroleum ether (1:20). The collected fractions were combined and concentrated. This resulted in 170 mg (33.69%) of 2-bromo-6-(2-fluoropropan-2-yl)pyridine as light yellow oil. LC-MS-1 (ES, m/z): 218 [M+1]$^+$ Synthesis of 1-[6-(2-fluoropropan-2-yl)pyridin-2-yl]-6-(methylsulfanyl)-2-(propan-2-yl)-1H,2H,3H-pyrazolo[3,4-d]pyrimidin-3-one: Into a 40-mL vial purged and maintained with an inert atmosphere of nitrogen, was placed 2-bromo-6-(2-fluoropropan-2-yl)pyridine (150.00 mg, 0.688 mmol, 1.00 equiv), 6-(methylsulfanyl)-2-(propan-2-yl)-1H,2H,3H-pyrazolo[3,4-d]pyrimidin-3-one (154.27 mg, 0.688 mmol, 1.00 equiv), dioxane (10.00 mL), K$_2$CO$_3$ (285.20 mg, 2.064 mmol, 3 equiv), CuI (131.00 mg, 0.688 mmol, 1 equiv), N,N-dimethylethane-1,2-diamine (60.53 mg, 0.688 mmol, 1.00 equiv). The resulting solution was stirred for 4 h at 95 degrees C. in an oil bath. The solids were filtered out. The resulting mixture was concentrated under vacuum. The residue was applied onto a silica gel column and eluted with ethyl acetate/petroleum ether (1:3). The collected fractions were combined and concentrated. This resulted in 100 mg (40.22%) of 1-[6-(2-fluoropropan-2-yl)pyridin-2-yl]-6-(methylsulfanyl)-2-(propan-2-yl)-1H,2H,3H-pyrazolo[3,4-d]pyrimidin-3-one as colorless oil. LC-MS-2 (ES, m/z): 362[M+1]$^+$ Synthesis of 1-[6-(2-fluoropropan-2-yl)pyridin-2-yl]-6-methanesulfinyl-2-(propan-2-yl)-1H,2H,3H-pyrazolo[3,4-d]pyrimidin-3-one: Into a 40-mL vial, was placed 1-[6-(2-fluoropropan-2-yl) pyridin-2-yl]-6-(methylsulfanyl)-2-(propan-2-yl)-1H, 2H, 3H-pyrazolo[3, 4-d] pyrimidin-3-one (50.00 mg, 0.138 mmol, 1.00 equiv), toluene (5.00 mL), m-CPBA (26.26 mg, 0.152 mmol, 1.10 equiv). The resulting solution was stirred for overnight at room temperature. The resulting mixture was concentrated. This resulted in 52.3 mg (crude) of 1-[6-(2-fluoropropan-2-yl)pyridin-2-yl]-6-methanesulfinyl-2-(propan-2-yl)-1H,2H,3H-pyrazolo[3,4-d]pyrimidin-3-one as a white solid. LC-MS-3 (ES, m/z): 378 [M+1]$^+$ Synthesis of 1-(6-(2-fluoropropan-2-yl)pyridin-2-yl)-2-isopropyl-6-((4-(4-methylpiperazin-1-yl)phenyl)amino)-1,2-dihydro-3H-pyrazolo[3,4-d]pyrimidin-3-one: Into a 40-mL vial, was placed 1-[6-(2-fluoropropan-2-yl)pyridin-2-yl]-6-methanesulfinyl-2-(propan-2-yl)-1H,2H,3H-pyrazolo[3,4-d]pyrimidin-3-one (52.30 mg, 0.139 mmol, 1.00 equiv), toluene (5.00 mL), DIEA (53.73 mg, 0.416 mmol, 3 equiv), 4-(4-methylpiperazin-1-yl)aniline (26.50 mg, 0.139 mmol, 1.00 equiv). The resulting solution was stirred for 4 h at 35 degrees C. in an oil bath. The resulting mixture was concentrated under vacuum. The residue was applied onto a silica gel column and eluted with ethyl acetate/petroleum ether (1:1). The collected fractions were combined and concentrated under vacuum. This resulted in 20 mg (28.60%) of 1-(6-(2-fluoropropan-2-yl)pyridin-2-yl)-2-isopropyl-6-((4-(4-methylpiperazin-1-yl)phenyl)amino)-1,2-dihydro-3H-pyrazolo[3,4-d]pyrimidin-3-one as a yellow solid. LC-MS-0 (ES, m/z): 505[M+1], $^1$H-NMR-0 (300 MHz, DMSO-d6, ppm) δ 10.13 (s, 1H), 8.76 (s, 1H), 8.16 (t, J=7.8 Hz, 1H), 7.86 (d, J=8.1 Hz, 1H), 7.69-7.48 (m, 3H), 6.92 (d, J=9.0 Hz, 2H), 4.16-4.12 (m, 1H), 3.16-3.05 (m, 4H), 2.49-2.46 (m, 4H), 2.23 (s, 3H), 1.71 (s, 3H), 1.63 (s, 3H), 1.38 (d, J=6.9 Hz, 6H).

Example 14: Preparation of 6-[[4-(4-methylpiperazin-1-yl)phenyl]amino]-2-(propan-2-yl)-1-(pyridin-2-yl)-1H,2H,3H-pyrazolo[3,4-d]pyrimidin-3-one Synthesis of 6-(methylsulfanyl)-2-(propan-2-yl)-1-(pyridin-2-yl)-1H,2H,3H-pyrazolo[3,4-d]pyrimidin-3-one: Into a 40-mL round-bottom flask purged and maintained with an inert atmosphere of nitrogen, was placed 6-(methylsulfanyl)-2-(propan-2-yl)-1H,2H,3H-pyrazolo[3,4-d]pyrimidin-3-one (250.00 mg, 1.115 mmol, 1.00 equiv), dioxane (5.00 mL), 2-bromopyridine (176.12 mg, 1.115 mmol, 1.00 equiv), methyl[2-(methylamino)ethyl]amine (29.48 mg, 0.334 mmol, 0.30 equiv), CuI (127.37 mg, 0.669 mmol, 0.60 equiv), Cs$_2$CO$_3$ (1.09 g, 3.344 mmol, 3.00 equiv). The resulting solution was stirred overnight at 90 degrees C. in an oil bath. The reaction mixture was cooled to room temperature. The resulting mixture was concentrated under vacuum. The residue was applied onto a silica gel column with ethyl acetate/petroleum ether (1:1). This resulted in 120 mg (35.72%) of 6-(methylsulfanyl)-2-(propan-2-yl)-1-(pyridin-2-yl)-1H,2H,3H-pyrazolo[3,4-d]pyrimidin-3-one as yellow oil. $^1$H NMR (300 MHz, CDCl$_3$-d, ppm) δ 8.90 (s, 1H), 8.56 (ddd, J=4.9, 1.9, 0.9 Hz, 1H), 7.93 (ddd, J=8.1, 7.3, 1.9 Hz, 1H), 7.80 (dt, J=8.2, 1.0 Hz, 1H), 7.32 (ddd, J=7.4, 4.9, 1.1 Hz, 1H), 2.56 (s, 3H), 1.50 (d, J=6.9 Hz, 6H).

Synthesis of 6-[[4-(4-methylpiperazin-1-yl)phenyl]amino]-2-(propan-2-yl)-1-(pyridin-2-yl)-1H,2H,3H-pyrazolo[3,4-d]pyrimidin-3-one: Into a 40-mL Vial, was placed 6-(methylsulfanyl)-2-(propan-2-yl)-1-(pyridin-2-yl)-1H,2H,3H-pyrazolo[3,4-d]pyrimidin-3-one (60.00 mg, 0.199 mmol, 1.00 equiv), toluene (5.00 mL), m-CPBA (41.00 mg, 0.238 mmol, 1.19 equiv), the resulting solution was stirred for 3 h at 40 degrees C. in an oil bath. To the above solution was added DIEA (77.00 mg, 0.596 mmol, 2.99 equiv), 4-(4-methylpiperazin-1-yl)aniline (38.08 mg, 0.199 mmol, 1.00 equiv). The resulting solution was stirred overnight at 40 degrees C. in an oil bath. The reaction mixture was cooled. The resulting mixture was concentrated under vacuum. The crude product was purified by Prep-HPLC with the following conditions (2#SHIMADZU (HPLC-01)): Column, XBridge Prep C18 OBD Column, 5 um, 19*150 mm; mobile phase, ACN and Water (0.05% NH$_3$.H$_2$O) (20% Phase B up to 75% in 1 min, up to 95% in 7 min, hold 95% in 1 min, down to 20% in 1 min); Detector, 254/220 nm. This resulted in 30 mg (33.90%) of 6-[[4-(4-methylpiperazin-1-yl)phenyl]amino]-2-(propan-2-yl)-1-(pyridin-2-yl)-1H,2H,3H-pyrazolo[3,4-d]pyrimidin-3-one as a light green solid. LC-MS (ES, m/z): M+1=445, R,T=1.941 min. $^1$H NMR (300 MHz, DMSO-d$_6$, ppm) δ 10.09 (s, 1H), 8.77 (s, 1H), 8.63-8.50 (m, 1H), 8.12 (d, J=8.2 Hz, 1H), 7.81 (d, J=8.1 Hz, 1H), 7.68-7.34 (m, 3H), 6.98-6.72 (m, 2H), 4.17 (p, J=6.8 Hz, 1H), 3.22-2.98 (m, 4H), 2.45 (t, J=5.0 Hz, 3H), 2.23 (s, 3H), 1.31 (d, J=6.7 Hz, 6H).

Example 15: Preparation of 1-(6-cyclopropylpyridin-2-yl)-2-isopropyl-6-((4-(4-methylpiperazin-1-yl)phenyl)amino)-1,2-dihydro-3H-pyrazolo[3,4-d]pyrimidin-3-one Synthesis of 2-bromo-6-cyclopropylpyridine: Into a 40-mL vial purged and maintained with an inert atmosphere of nitrogen, was placed pyridine, 2,6-dibromo- (1.00 g, 4.221 mmol, 1.00 equiv), THF (10.00 mL), Pd(PPh$_3$)$_4$ (246.00 mg, 0.213 mmol, 0.05 equiv). This was followed by the addition of bromo(cyclopropyl)zinc (10.20 mL, 5.100 mmol, 1.21 equiv) dropwise with stirring at 25 degrees C. The resulting solution was stirred for 5 hr at 50 degrees C. in an oil bath. The reaction mixture was cooled to room temperature. The resulting solution was poured into 200 mL of aqueous NaHCO$_3$. The resulting solution was extracted with 2×100 mL of ethyl acetate and the organic layers combined. The resulting mixture was washed with 1×500 ml of brine. The mixture was dried over anhydrous sodium sulfate. The solids were filtered out. The resulting mixture was concentrated under vacuum. The residue was applied onto a silica gel column with ethyl acetate/petroleum ether (1:13). This resulted in 590 mg (47.99%) of 2-bromo-6-cyclopropylpyridine as light yellow oil. LC-MS (ES, m/z): M+1=198

Synthesis of 1-(6-cyclopropylpyridin-2-yl)-2-isopropyl-6-(methylsulfanyl)pyrazolo[3,4-d]pyrimidin-3-one: Into a 40-mL vial purged and maintained with an inert atmosphere of nitrogen, was placed 2-isopropyl-6-(methylsulfanyl)-1H-pyrazolo[3,4-d]pyrimidin-3-one (489.00 mg, 2.180 mmol, 1.00 equiv), dioxane (10 mL), 2-bromo-6-cyclopropylpyridine (430.00 mg, 2.171 mmol, 1.00 equiv), methyl[2-(methylamino)ethyl]amine (192.00 mg, 2.178 mmol, 1.00 equiv), CuI (414.00 mg, 2.174 mmol, 1.00 equiv), K$_2$CO$_3$ (903.00 mg, 6.534 mmol, 3.00 equiv). The resulting solution was stirred for 3 hr at 90 degrees C. in an oil bath. The reaction mixture was cooled to room temperature. The resulting mixture was concentrated under vacuum. The residue was applied onto a silica gel column with ethyl acetate/petroleum ether (1:1). This resulted in 300 mg (40.30%) of 1-(6-cyclopropylpyridin-2-yl)-2-isopropyl-6-(methylsulfanyl)pyrazolo[3,4-d]pyrimidin-3-one as light yellow oil. LC-MS (ES, m/z): M+1=342

Synthesis of 1-(6-cyclopropylpyridin-2-yl)-2-isopropyl-6-((4-(4-methylpiperazin-1-yl)phenyl)amino)-1,2-dihydro-3H-pyrazolo[3,4-d]pyrimidin-3-one: Into a 40-mL vial, was placed 1-(6-cyclopropylpyridin-2-yl)-2-isopropyl-6-(methylsulfanyl)pyrazolo[3,4-d]pyrimidin-3-one (300.00 mg, 0.879 mmol, 1.00 equiv), toluene (10.00 mL), m-CPBA (181.00 mg, 1.049 mmol, 1.19 equiv), the resulting solution was stirred for 3 h at 40 degrees C. in an oil bath. To the above solution was added DIEA (341.00 mg, 2.638 mmol, 3.00 equiv), 4-(4-methylpiperazin-1-yl)aniline (168.00 mg, 0.878 mmol, 1.00 equiv). The resulting solution was stirred overnight at 40 degrees C. in an oil bath. The reaction mixture was cooled to room temperature. The resulting mixture was concentrated under vacuum. The residue was applied onto a silica gel column with dichloromethane/methanol (10:1). The crude product was purified by Flash-Prep-HPLC with the following conditions (IntelFlash-1): Column, C18 reversed phase column; mobile phase, water (0.05% $NH_3.H_2O$) and $CH_3CN$ (20% $CH_3CN$ increasing to 70% within 15 min); Detector, 254/220 nm. This resulted in 180 mg (42.27%) of 1-(6-cyclopropylpyridin-2-yl)-2-isopropyl-6-((4-(4-methylpiperazin-1-yl)phenyl)amino)-1,2-dihydro-3H-pyrazolo[3,4-d]pyrimidin-3-one as a yellow solid. LC-MS (ES, m/z): M+1=485, $^1$H NMR (300 MHz, DMSO-d6, ppm) δ 10.07 (s, 1H), 8.74 (s, 1H), 7.93 (t, J=7.8 Hz, 1H), 7.57 (t, J=8.8 Hz, 3H), 7.32 (d, J=7.6 Hz, 1H), 7.07-6.75 (m, 2H), 4.10 (p, J=6.8 Hz, 1H), 3.09 (t, J=5.0 Hz, 4H), 2.49-2.42 (m, 4H), 2.23 (s, 3H), 2.20-2.11 (m, 1H), 1.34 (d, J=6.8 Hz, 6H), 1.10-0.75 (m, 4H).

Example 16: Preparation of 1-[6-(1,1-difluoroethyl)pyridin-2-yl]-6-[[4-(4-methylpiperazin-1-yl)phenyl]amino]-2-(propan-2-yl)-1H,2H,3H-pyrazolo[3,4-d]pyrimidin-3-one Synthesis of 2-bromo-6-(1,1-difluoroethyl)pyridine: Into a 250-mL round-bottom flask, was placed 1-(6-bromopyridin-2-yl)ethan-1-one (3.00 g, 14.997 mmol, 1.00 equiv), DCM (100.00 mL), DAST (8.49 g, 52.671 mmol, 3.51 equiv). The resulting solution was stirred overnight at 25 degrees C. The reaction was then quenched by the addition of 500 mL of aqueous $NaHCO_3$. The resulting solution was extracted with 2×200 mL of dichloromethane and the organic layers were combined. The resulting mixture was washed with 1×500 ml of brine. The mixture was dried over anhydrous sodium sulfate and concentrated under vacuum. The residue was applied onto a silica gel column with petroleum ether. This resulted in 410 mg (12.31%) of 2-bromo-6-(1,1-difluoroethyl)pyridine as yellow oil. $^1$H-NMR (300 MHz, $CDCl_3$-d, ppm): δ 7.85-7.46 (m, 3H), 2.04 (t, J=18.7 Hz, 3H).

Synthesis of 1-[6-(1,1-difluoroethyl)pyridin-2-yl]-6-(methylsulfanyl)-2-(propan-2-yl)-1H,2H,3H-pyrazolo[3,4-d]pyrimidin-3-one: Into a 40-mL round-bottom flask purged and maintained with an inert atmosphere of nitrogen, was placed 6-(methylsulfanyl)-2-(propan-2-yl)-1H,2H,3H-pyrazolo[3,4-d]pyrimidin-3-one (250.00 mg, 1.115 mmol, 1.00 equiv), dioxane (5.00 mL), 2-bromo-6-(1,1-difluoroethyl)pyridine (247.00 mg, 1.112 mmol, 1.00 equiv), methyl[2-(methylamino)ethyl]amine (30.00 mg, 0.340 mmol, 0.31 equiv), CuI (128.00 mg, 0.672 mmol, 0.60 equiv), $Cs_2CO_3$ (1.09 g, 3.345 mmol, 3.00 equiv). The resulting solution was stirred overnight at 90 degrees C. in an oil bath. The reaction mixture was cooled. The resulting mixture was concentrated under vacuum. The residue was applied onto a silica gel column with ethyl acetate/petroleum ether (1:1). This resulted in 140 mg (34.37%) of 1-[6-(1,1-difluoroethyl)pyridin-2-yl]-6-(methylsulfanyl)-2-(propan-2-yl)-1H,2H,3H-pyrazolo[3,4-d]pyrimidin-3-one as yellow oil.

Synthesis of 1-[6-(1,1-difluoroethyl)pyridin-2-yl]-6-[[4-(4-methylpiperazin-1-yl)phenyl]amino]-2-(propan-2-yl)-1H,2H,3H-pyrazolo[3,4-d]pyrimidin-3-one: Into a 40-mL vial, was placed 1-[6-(1,1-difluoroethyl)pyridin-2-yl]-6-(methylsulfanyl)-2-(propan-2-yl)-1H,2H,3H-pyrazolo[3,4-d]pyrimidin-3-one (84.00 mg, 0.230 mmol, 1.00 equiv), toluene (5.00 mL), m-CPBA (47.00 mg, 0.272 mmol, 1.18 equiv), the resulting solution was stirred for 3 h at 40 degrees C. in an oil bath. To the above solution was added DIEA (89.00 mg, 0.689 mmol, 3.00 equiv), 4-(4-methylpiperazin-1-yl)aniline (44.00 mg, 0.230 mmol, 1.00 equiv). The resulting solution was stirred overnight at 40 degrees C. in an oil bath. The reaction mixture was cooled. The resulting mixture was concentrated under vacuum. The crude product was purified by Prep-HPLC with the following conditions (2#SHIMADZU (HPLC-01)): Column, XBridge Prep C18 OBD Column, 5 um, 19*150 mm; mobile phase, ACN and Water (0.05% $NH_3.H_2O$) (20% Phase B up to 75% in 1 min, up to 95% in 7 min, hold 95% in 1 min, down to 20% in 1 min); Detector, 254/220 nm. This resulted in 40 mg (34.21%) of 1-[6-(1,1-difluoroethyl)pyridin-2-yl]-6-[[4-(4-methylpiperazin-1-yl)phenyl]amino]-2-(propan-2-yl)-1H,2H,3H-pyrazolo[3,4-d]pyrimidin-3-one as a yellow solid. LC-MS (ES, m/z): M+1=509, $^1$H NMR (300 MHz, DMSO-d6, ppm): δ 10.17 (s, 2H), 8.78 (s, 1H), 8.28 (t, J=8.0 Hz, 1H), 8.05 (d, J=8.1 Hz, 1H), 7.69 (d, J=7.6 Hz, 1H), 7.55 (d, J=8.3 Hz, 2H), 6.92 (d, J=8.8 Hz, 2H), 4.15 (p, J=6.9 Hz, 1H), 3.18-3.03 (m, 4H), 2.46 (t, J=4.9 Hz, 4H), 2.23 (s, 3H), 2.01 (t, J=19.1 Hz, 3H), 1.37 (d, J=6.8 Hz, 6H).

Example 17: Preparation of 2-cyclopropyl-1-[6-(2-fluoropropan-2-yl)pyridin-2-yl]-6-[[4-(4-methylpiperazin-1-yl)phenyl]amino]-1H,2H,3H-pyrazolo[3,4-d]pyrimidin-3-one Synthesis of N-cyclopropyl-N-oxo(tert-butoxy)carbohydrazide: Into a 250-mL 3-necked round-bottom flask, was placed tert-butyl N-cyclopropylcarbamate (4.80 g, 30.532 mmol, 1.0 equiv), ACN (100.00 mL, 1902.470 mmol, 62.31 equiv), Py (4.83 g, 61.14 mmol, 2.0 equiv). This was followed by the addition of Nitrosonium tetrafluoroborate (4.70 g, 30.532 mmol, 1.0=equiv), in portions at 0 degrees C. The resulting solution was stirred for overnight at room temperature. The reaction was then quenched by the addition of 100 mL of water. The resulting solution was extracted with 2×100 mL of ethyl acetate. The resulting mixture was washed with 2×100 ml of Brine. The mixture was dried over anhydrous sodium sulfate and concentrated. The residue was applied onto a silica gel column and eluted with ethyl acetate/petroleum ether (0:1-1:10). This resulted in 1.5 g (26.38%) of N-cyclopropyl-N-oxo(tert-butoxy)carbohydrazide as yellow oil. LC-MS-1 (ES, m/z): M+1=187. $^1$H-NMR-1 (300 MHz, $CDCl_3$, ppm): δ 2.36-2.31 (m, 1H), 1.65 (s, 9H), 1.10-1.03 (m, 2H), 0.61-0.51 (m, 2H).

Synthesis of N-cyclopropyl(tert-butoxy)carbohydrazide: Into a 40-mL round-bottom flask, was placed N-cyclopropyl-N-oxo(tert-butoxy)carbohydrazide (1.50 g, 8.055 mmol, 1.00 equiv), EtOH (10.00 mL), $H_2O$ (10.00 mL), $NH_4Cl$ (4.31 g, 80.554 mmol, 10.00 equiv). This was followed by the addition of Zn (5.27 g, 80.554 mmol, 10.00 equiv), in portions at 0 degrees C. The resulting solution was stirred for overnight at room temperature. The solids were filtered out. The resulting solution was extracted with 2×20 mL of ethyl acetate concentrated. The residue was applied onto a silica gel column and eluted with ethyl acetate/petroleum ether (0:1-1:0). This resulted in 300 mg (21.62%) of N-cyclopropyl(tert-butoxy)carbohydrazide as a white oil. $^1$H-NMR-2 (300 MHz, CDCl$_3$, ppm): δ 2.83-2.78 (m, 1H), 1.37 (s, 9H), 0.66-0.59 (m, 4H).

Synthesis of ethyl 4-([N-cyclopropyl[(tert-butoxy)carbonyl] amino]amino)-2-(methylsulfanyl)pyrimidine-5-carboxylate: Into a 8-mL round-bottom flask, was placed N-cyclopropyl(tert-butoxy)carbohydrazide (222.06 mg, 1.289 mmol, 1 equiv), ethyl 4-chloro-2-(methylsulfanyl)pyrimidine-5-carboxylate (300.00 mg, 1.289 mmol, 1.00 equiv), THF (5.00 mL), DIEA (416.59 mg, 3.22 mmol, 2.5 equiv). The resulting solution was stirred for overnight at 70 degrees C. The resulting mixture was concentrated. The residue was applied onto a silica gel column and eluted with ethyl acetate/petroleum ether (0:1-1:1). This resulted in 200 mg (42.10%) of ethyl 4-([N-cyclopropyl[(tert-butoxy)carbonyl] amino]amino)-2-(methylsulfanyl)pyrimidine-5-carboxylate as a white solid. LC-MS-3 (ES, m/z): M+1=369

Synthesis of ethyl 4-(2-cyclopropylhydrazin-1-yl)-2-(methylsulfanyl) pyrimidine-5-carboxylate: Into a 8-mL round-bottom flask, was placed ethyl 4-([N-cyclopropyl[(tert-butoxy)carbonyl]amino] amino)-2-(methylsulfanyl) pyrimidine-5-carboxylate (200.00 mg, 0.543 mmol, 1.00 equiv), DCM (3 mL), TFA (618.93 mg, 5.428 mmol, 10.00 equiv). The resulting solution was stirred for overnight at room temperature. The resulting mixture was concentrated. This resulted in 160 mg (109.85%) of ethyl 4-(2-cyclopropylhydrazin-1-yl)-2-(methylsulfanyl) pyrimidine-5-carboxylate as a yellow crude solid. LC-MS-4 (ES, m/z): M+1=255

Synthesis of 2-cyclopropyl-6-(methylsulfanyl)-1H,2H, 3H-pyrazolo[3,4-d]pyrimidin-3-one: Into a 8-mL round-bottom flask, was placed ethyl 4-(2-cyclopropylhydrazin-1-yl)-2-(methylsulfanyl) pyrimidine-5-carboxylate (160.00 mg, 0.596 mmol, 1.00 equiv), EtOH (2 mL). This was followed by the addition of a solution of NaOH (143.09 mg, 3.578 mmol, 6.00 equiv) in H$_2$O (1 mL) dropwise with stirring at 0 degrees C. The resulting solution was stirred for 1 h at room temperature. The pH value of the solution was adjusted to 7 with HCl (1 mol/L). The resulting mixture was concentrated. The residue was applied onto a silica gel column and eluted with dichloromethane/methanol (1:0-10:1). This resulted in 100 mg (75.45%) of 2-cyclopropyl-6-(methylsulfanyl)-1H,2H,3H-pyrazolo[3,4-d]pyrimidin-3-one as a yellow solid. $^1$H-NMR-5 (300 MHz, d6-DMSO, ppm): δ 8.73-8.64 (m, 1H), 3.51-3.17 (m, 4H), 1.24-1.16 (m, 1H), 1.08-0.83 (m, 4H).

Synthesis of 2-bromo-6-(2-fluoropropan-2-yl)pyridine: Into a 100-mL 3-necked round-bottom flask, was placed 2-(6-bromopyridin-2-yl)propan 2-ol (5.00 g, 23.140 mmol, 1.00 equiv), DCM (50.00 mL). This was followed by the addition of DAST (11.19g, 0.069 mmol, 3 equiv)dropwise with stirring at −78 degrees C. The resulting solution was stirred for overnight at room temperature. The reaction was then quenched by the addition of 100 mL of NaHCO$_3$ (2 mol/L). The resulting solution was extracted with 3×100 mL of dichloromethane concentrated. The residue was applied onto a silica gel column and eluted with ethyl acetate/ petroleum ether (1:20). The collected fractions were combined and concentrated under vacuum. This resulted in 1 g (19.82%) of 2-bromo-6-(2-fluoropropan-2-yl)pyridine as colorless oil. LC-MS-1 (ES, m/z): 218[M+1]

Synthesis of 2-cyclopropyl-1-[6-(2-fluoropropan-2-yl)pyridin-2-yl]-6-(methylsulfanyl)-1H,2H,3H-pyrazolo[3,4-d]pyrimidin-3-one: Into a 40-mL vial purged and maintained with an inert atmosphere of nitrogen, was placed 2-bromo-6-(2-fluoropropan-2-yl)pyridine (146.00 mg, 0.670 mmol, 1.00 equiv), dioxane (5.00 mL), 2-cyclopropyl-6-(methylsulfanyl)-1H,2H,3H-pyrazolo[3,4-d]pyrimidin-3-one (148.81 mg, 0.670 mmol, 1 equiv), K$_2$CO$_3$ (277.59 mg, 2.009 mmol, 3 equiv), Cu 1 (127.51 mg, 0.670 mmol, 1 equiv), N1,N2-dimethylethane-1,2-diamine (58.92 mg, 0.670 mmol, 1 equiv). The resulting solution was stirred for 4 h at 95 degrees C. in an oil bath. The solids were filtered out. The resulting solution was extracted with 3×20 mL of ethyl acetate concentrated. The residue was applied onto a silica gel column and eluted with ethyl acetate/petroleum ether (1:1). The collected fractions were combined and concentrated under vacuum. This resulted in 60 mg (24.93%) of 2-cyclopropyl-1-[6-(2-fluoropropan-2-yl)pyridin-2-yl]-6-(methylsulfanyl)-1H,2H,3H-pyrazolo[3,4-d]pyrimidin-3-one as a white solid. LC-MS-2 (ES, m/z): 359 [M+1]

Synthesis of 2-cyclopropyl-1-[6-(2-fluoropropan-2-yl) pyridin-2-yl]-6-[[4-(4-methylpiperazin-1-yl)phenyl]amino]-1H,2H,3H-pyrazolo[3,4-d]pyrimidin-3-one: Into a 40-mL vial, was placed 2-cyclopropyl-1-[6-(2-fluoropropan-2-yl) pyridin-2-yl]-6-(methylsulfanyl)-1H,2H,3H-pyrazolo[3,4-d]pyrimidin-3-one (50.00 mg, 0.139 mmol, 1.00 equiv), toluene (5.00 mL), m-CPBA (26.41 mg, 0.153 mmol, 1.1 equiv), The resulting solution was stirred for 3 h at room temperature. 4-(4-methylpiperazin-1-yl)aniline (29.27 mg, 0.153 mmol, 1.10 equiv), DIEA (53.94 mg, 0.417 mmol, 3 equiv). The resulting solution was stirred for overnight at room temperature. The resulting mixture was concentrated. The residue was applied onto a silica gel column and eluted with dichloromethane/methanol (10:1). The collected fractions were combined and concentrated under vacuum. This resulted in 40 mg (57.21%) of 2-cyclopropyl-1-[6-(2-fluoropropan-2-yl)pyridin-2-yl]-6-[[4-(4-methylpiperazin-1-yl) phenyl]amino]-1H,2H,3H-pyrazolo[3,4-d]pyrimidin-3-one as a yellow solid. LC-MS-0 (ES, m/z): 503[M+1], $^1$H-NMR-0 (300 MHz, DMSO-d6, ppm) δ 10.04 (s, 1H), 8.75 (s, 1H), 8.17 (t, J=7.8 Hz, 1H), 7.91-7.80 (m, 1H), 7.67-7.46 (m, 3H), 6.92 (d, J=8.9 Hz, 2H), 3.20 (t, J=5.1 Hz, 1H), 3.15-3.05 (m, 4H), 2.46 (d, J=5.4 Hz, 4H), 2.24 (s, 3H), 1.71 (s, 3H), 1.64 (s, 3H), 0.82 (d, J=5.4 Hz, 4H).

Example 18: Preparation of 2-cyclopropyl-1-[6-(1, 1-difluoroethyl)pyridin-2-yl]-6-[[4-(4-methylpiperazin-1-yl)phenyl]amino]pyrazolo[3,4-d]pyrimidin-3-one Synthesis of 2-cyclopropyl-1-[6-(1,1-difluoroethyl)pyridin-2-yl]-6-(methylsulfanyl)-1H,2H,3H-pyrazolo[3,4-d]pyrimidin-3-one: Into a 40-mL vial purged and maintained with an inert atmosphere of nitrogen, was placed 2-cyclopropyl-6-(methylsulfanyl)-1H,2H,3H-pyrazolo[3,4-d]pyrimidin-3-one (150.00 mg, 0.675 mmol, 1.00 equiv), dioxane (5.00 mL), 2-bromo-6-(1,1-difluoroethyl)pyridine (150.00 mg, 0.676 mmol, 1.00 equiv), methyl[2-(methylamino)ethyl]amine (60.00 mg, 0.681 mmol, 1.01 equiv), CuI (128.00 mg, 0.672 mmol, 1.00 equiv), K$_2$CO$_3$ (280.00 mg, 2.026 mmol, 3.00 equiv). The resulting solution was stirred for 6 hr at 95 degrees C. in an oil bath. The reaction mixture was cooled to room temperature. The resulting mixture was concentrated under vacuum. The residue was applied onto a silica gel column with ethyl acetate/petroleum ether (1:1). This resulted in 165 mg (67.28%) of 2-cyclopropyl-1-[6-(1,1-difluoroethyl)pyridin-2-yl]-6-(methylsulfanyl)-1H,2H,3H-pyrazolo[3,4-d]pyrimidin-3-one as a white solid. $^1$H NMR (300 MHz, Chloroform-d, ppm) δ 8.92 (s, 1H), 8.10-7.97 (m, 2H), 7.64 (dd, J=6.4, 2.1 Hz, 1H), 3.58-3.37 (m, 1H), 2.60 (s, 3H), 2.02 (t, J=18.6 Hz, 3H), 1.07-0.83 (m, 4H).

Synthesis of 2-cyclopropyl-1-[6-(1,1-difluoroethyl)pyridin-2-yl]-6-[[4-(4-methylpiperazin-1-yl)phenyl]amino]pyrazolo[3,4-d]pyrimidin-3-one: Into a 40-mL vial, was placed 2-cyclopropyl-1-[6-(1,1-difluoroethyl)pyridin-2-yl]-6-(methylsulfanyl)pyrazolo[3,4-d]pyrimidin-3-one (160.00 mg, 0.440 mmol, 1.00 equiv), toluene (5.00 mL), m-CPBA (90.00 mg, 0.522 mmol, 1.18 equiv), the resulting solution was stirred for 3 h at 40 degrees C. in an oil bath. To the above solution was added DIEA (170.00 mg, 1.315 mmol, 2.99 equiv), 4-(4-methylpiperazin-1-yl)aniline (84.00 mg, 0.439 mmol, 1.00 equiv). The resulting solution was stirred overnight at 40 degrees C. in an oil bath. The reaction mixture was cooled to room temperature. The resulting mixture was concentrated under vacuum. The crude product was purified by Prep-HPLC with the following conditions (SHIMADZU (HPLC-01)): Column, XBridge Prep C18 OBD Column, 5 um, 19*150 mm; mobile phase, ACN and Water (0.05% NH$_3$.H$_2$O) (20% Phase B up to 75% in 1 min, up to 95% in 7 min, hold 95% in 1 min, down to 20% in 1 min); Detector, 254/220 nm. This resulted in 90 mg (40.35%) of 2-cyclopropyl-1-[6-(1,1-difluoroethyl)pyridin-2-yl]-6-[[4-(4-methylpiperazin-1-yl)phenyl]amino]pyrazolo[3,4-d]pyrimidin-3-one as a yellow solid. LC-MS: (ES, m/z): M+1=507, $^1$H NMR (300 MHz, DMSO-d6, ppm) δ 10.10 (s, 1H), 8.76 (s, 1H), 8.29 (t, J=8.0 Hz, 1H), 8.05 (d, J=8.2 Hz, 1H), 7.73-7.65 (m, 1H), 7.56 (d, J=8.4 Hz, 2H), 6.93 (d, J=8.8 Hz, 2H), 3.20 (s, 1H), 3.12-3.09 (m, 4H), 2.50-2.45 (m, 4H), 2.23 (s, 3H), 2.02 (t, J=19.1 Hz, 3H), 0.98-0.71 (m, 4H).

Example 19: Preparation of 2-cyclopropyl-1-(6-cyclopropylpyridin-2-yl)-6-[[4-(4-methylpiperazin-1-yl)phenyl]amino]pyrazolo[3,4-d]pyrimidin-3-one Synthesis of 2-cyclopropyl-1-(6-cyclopropylpyridin-2-yl)-6-(methylsulfanyl)-1H,2H,3H-pyrazolo[3,4-d]pyrimidin-3-one: Into a 40-mL vial purged and maintained with an inert atmosphere of nitrogen, was placed 2-cyclopropyl-6-(methylsulfanyl)-1H,2H,3H-pyrazolo[3,4-d]pyrimidin-3-one (101.00 mg, 0.454 mmol, 1.00 equiv), dioxane (5.00 mL, 59.020 mmol, 129.89 equiv), 2-bromo-6-cyclopropylpyridine (90.00 mg, 0.454 mmol, 1.00 equiv), methyl[2-(methylamino)ethyl]amine (40.00 mg, 0.454 mmol, 1.00 equiv), CuI (87.00 mg, 0.457 mmol, 1.01 equiv), K$_2$CO$_3$ (189.00 mg, 1.368 mmol, 3.01 equiv). The resulting solution was stirred overnight at 95 degrees C. in an oil bath. The reaction mixture was cooled to room temperature. The resulting mixture was concentrated under vacuum. The residue was applied onto a silica gel column with ethyl acetate/petroleum ether (1:1). This resulted in 95 mg (61.60%) of 2-cyclopropyl-1-(6-cyclopropylpyridin-2-yl)-6-(methylsulfanyl)-1H,2H,3H-pyrazolo[3,4-d]pyrimidin-3-one as a white solid. $^1$H NMR (300 MHz, Chloroform-d, ppm) δ 8.89 (s, 1H), 7.75 (t, J=7.8 Hz, 1H), 7.58 (dd, J=8.0, 0.9 Hz, 1H), 7.18 (dd, J=7.6, 0.9 Hz, 1H), 3.38-3.31 (m, 1H), 2.58 (s, 3H), 2.11-2.00 (m, 1H), 1.06-0.92 (m, 8H).

Synthesis of 2-cyclopropyl-1-(6-cyclopropylpyridin-2-yl)-6-[[4-(4-methylpiperazin-1-yl)phenyl]amino]pyrazolo[3,4-d]pyrimidin-3-one: Into a 40-mL vial, was placed 2-cyclopropyl-1-(6-cyclopropylpyridin-2-yl)-6-(methylsulfanyl)pyrazolo[3,4-d]pyrimidin-3-one (95.00 mg, 0.280 mmol, 1.00 equiv), toluene (3.00 mL), m-CPBA (58.00 mg, 0.336 mmol, 1.20 equiv), the resulting solution was stirred for 3 h at 40 degrees C. in an oil bath. To the above solution was added DIEA (108.00 mg, 0.836 mmol, 2.99 equiv), 4-(4-methylpiperazin-1-yl)aniline (53.00 mg, 0.277 mmol, 0.99 equiv). The resulting solution was stirred overnight at 40 degrees C. in an oil bath. The resulting mixture was concentrated under vacuum. The crude product was purified by Prep-HPLC with the following conditions (2#SHIMADZU (HPLC-01)): Column, XBridge Prep C18 OBD Column, 5 um, 19*150 mm; mobile phase, ACN and Water (0.05% NH$_3$.H$_2$O) (20% Phase B up to 75% in 1 min, up to 95% in 7 min, hold 95% in 1 min, down to 20% in 1 min); Detector, 254/220 nm. This resulted in 50 mg (37.02%) of 2-cyclopropyl-1-(6-cyclopropylpyridin-2-yl)-6-[[4-(4-methylpiperazin-1-yl)phenyl]amino]pyrazolo[3,4-d]pyrimidin-3-one as a grey solid. LC-MS: (ES, m/z): M+1=483, $^1$H NMR (300 MHz, DMSO-d6, ppm) δ 10.00 (s, 1H), 8.72 (s, 1H), 7.94 (t, J=7.7 Hz, 1H), 7.57 (dd, J=9.1, 6.0 Hz, 3H), 7.42-7.13 (m, 1H), 6.90 (d, J=9.0 Hz, 2H), 3.21-2.93 (m, 5H), 2.48-2.42 (m, 4H), 2.23 (s, 3H), 2.20-2.12 (m, 1H), 1.03-0.87 (m, 4H), 0.83-0.77 (m, 4H).

The compounds below are prepared by methods substantially identical, similar, or analogous to those disclosed in above Schemes and Examples:

| Example | Chemical Name | m/z (MH$^+$) |
|---|---|---|
| Cpd-1 | (R)-6-((4-(3-(dimethylamino)pyrrolidin-1-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one | 569 |
| Cpd-2 | (S)-6-((4-(3-(dimethylamino)pyrrolidin-1-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one | 569 |
| Cpd-3 | 6-((4-fluorophenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one | 475 |
| Cpd-4 | 1-(6-cyclopropylpyridin-2-yl)-2-isopropyl-6-((4-(4-(2,2,2-trifluoroethyl)piperazin-1-yl)phenyl)amino)-1,2-dihydro-3H-pyrazolo[3,4-d]pyrimidin-3-one | 553 |
| Cpd-5 | 6-((4-(4-cyclopropylpiperazin-1-yl)phenyl)amino)-1-(6-cyclopropylpyridin-2-yl)-2-isopropyl-1,2-dihydro-3H-pyrazolo[3,4-d]pyrimidin-3-one | 511 |
| Cpd-6 | 1-(6-cyclopropylpyridin-2-yl)-6-((4-(4-ethylpiperazin-1-yl)phenyl)amino)-2-isopropyl-1,2-dihydro-3H-pyrazolo[3,4-d]pyrimidin-3-one | 499 |
| Cpd-7 | 1-(6-cyclopropylpyridin-2-yl)-2-isopropyl-6-((4-(piperidin-3-yl)phenyl)amino)-1,2-dihydro-3H-pyrazolo[3,4-d]pyrimidin-3-one | 470 |
| Cpd-8 | 2-cyclobutyl-6-((4-(4-methylpiperazin-1-yl)phenyl)amino)-1-(6-(1,1,1-trifluoro-2-methylpropan-2-yl)pyridin-2-yl)-1,2-dihydro-3H-pyrazolo[3,4-d]pyrimidin-3-one | 567 |
| Cpd-9 | 1-(6-(1,1-difluoroethyl)pyridin-2-yl)-2-isopropyl-6-((5-(4-methylpiperazin-1-yl)pyridin-2-yl)amino)-1,2-dihydro-3H-pyrazolo[4,3-c]pyridin-3-one | 509 |
| Cpd-10 | 2-isopropyl-6-((2-(oxetan-3-yl)-1,2,3,4-tetrahydroisoquinolin-6-yl)amino)-1-(6-(1,1,1-trifluoro-2-methylpropan-2-yl)pyridin-2-yl)-1,2-dihydro-3H-pyrazolo[3,4-d]pyrimidin-3-one | 568 |
| Cpd-11 | 2-isopropyl-6-((3-methyl-4-morpholinophenyl)amino)-1-(6-(1,1,1-trifluoro-2-methylpropan-2-yl)pyridin-2-yl)-1,2-dihydro-3H-pyrazolo[3,4-d]pyrimidin-3-one | 556 |

| Example | Chemical Name | m/z (MH+) |
|---|---|---|
| Cpd-12 | 6((4-(8-oxa-3-azabicyclo[3.2.1]octan-3-yl)phenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one | 568 |
| Cpd-13 | 6-((3-fluoro-4-morpholinophenyl)amino)-2-isopropyl-1-(6-(1,1,1-trifluoro-2-methylpropan-2-yl)pyridin-2-yl)-1,2-dihydro-3H-pyrazolo[3,4-d]pyrimidin-3-one | 560 |

Biological Example 1: Wee-1 Biochemical Assay

In determination of the Wee1 kinase activity, a synthetic peptide, Poly(Lys,Tyr) Hydrobromide (Lys:Tyr (4:1)) bought from Sigma was used as the substrate. The amount of the reaction mixture was 21.1 µL; and the composition of the reaction buffer was 50 mM Tris-HCl buffer (pH 7.4)/10 mM magnesium chloride/1 mM dithiothreitol. The purified Wee1 kinase, 2.5 µg of the substrate peptide, 10 µM of non-labeled adenosine triphosphate (ATP) and 1 µCi of [$\gamma$-$^{33}$P]-labeled ATP (2500 Ci/mmol or more) were added to it, and incubated at 30° C. for 30 minutes. Next, 10 µL of 350 mM phosphate buffer was added to the reaction mixture to stop the reaction. The substrate peptide was adsorbed by a P81 paper filter 96-well plate, then washed a few times with 130 mM phosphate buffer, and its radioactivity was counted with a liquid scintillation counter. The [$\gamma$-$^{33}$P]-labeled ATP was bought from Amersham Bioscience. To add the test compound to the reaction system, the compound was diluted with dimethylsulfoxide (DMSO) to prepare a series of dilutions. 1.1 µL of each dilution was added to the reaction system. As a control, 1.1 µL of DMSO was added to the reaction system. Such assays, carried out with a range of doses of test compounds, allow the determination of the Wee1 $IC_{50}$ of the compounds of the present invention The following table lists the Wee1 $IC_{50}$ values of another study for certain compounds of the invention.

| Compound | Wee1 $IC_{50}$ |
|---|---|
| AZD1775 | <1.5 nM |
| Example 11 | <1.5 nM |
| Example 13 | <1.5 nM |
| Example 15 | <1.5 nM |

Biological Example 2: In Vitro Cellular Anti-Proliferation Assay

Cell antiproliferation was assayed by PerkinElmer ATPlite™ Luminescence Assay System. Briefly, the various test cancer cell lines were plated at a density of about 1×10$^4$ cells per well in Costar 96-well plates, and were incubated with different concentrations of compounds for about 72 hours in medium supplemented with 5% FBS. One lyophilized substrate solution vial was then reconstituted by adding 5 mL of substrate buffer solution, and was agitated gently until the solution was homogeneous. About 50 µL of mammalian cell lysis solution was added to 100 µL of cell suspension per well of a microplate, and the plate was shaken for about five minutes in an orbital shaker at ~700 rpm. This procedure was used to lyse the cells and to stabilize the ATP. Next, 50 µL substrate solution was added to the wells and microplate was shaken for five minutes in an orbital shaker at ~700 rpm. Finally, the luminescence was measured by a PerkinElmer TopCount® Microplate Scintillation Counter. Such assays, carried out with a range of doses of test compounds, allowed the determination of the cellular anti-antiproliferative $IC_{50}$ of the compounds of the present invention. The following table lists the $IC_{50}$ values of several cancer cell lines (5% FBS) for certain compounds of the invention.

The following table lists the LoVo $IC_{50}$ values of another study for certain compounds of the invention.

| Compound | LoVo $IC_{50}$ | A498 $IC_{50}$ | SK-MES-1 $IC_{50}$ |
|---|---|---|---|
| AZD1775 | <0.3 uM | <0.5 uM | <0.25 uM |
| Example 11 | <0.3 uM | <0.5 uM | <0.25 uM |
| Example 13 | <0.3 uM | <0.5 uM | <0.25 uM |
| Example 15 | <0.3 uM | <0.5 uM | <0.25 uM |

Biological Example 3: Mice PK Study

The pharmacokinetics of compounds were evaluated in CD-1 mouse via Intravenous and Oral Administration. The iv dose was administered as a slow bolus in the Jugular vein, and oral doses were administered by gavage. The formulation for IV dosing is 5% DMSO in "20% HPBCD in water, and the PO formulation is 2.5% DMSO, 10% EtOH, 20% Cremphor EL, 67.5% D5W. The PK time point for the IV arm is 5, 15, 30 min, 1, 2, 4, 6, 8, 12, 24 hours post dose, and for PO arm is 15, 30 min, 1, 2, 4, 6, 8, 12, 24 hours post dose. Approximately 0.03 mL blood will be collected at each time point. Blood of each sample will be transferred into plastic micro centrifuge tubes containing EDTA-K2 and collect plasma within 15 min by centrifugation at 4000 g for 5 minutes in a 4° C. centrifuge. Plasma samples will be stored in polypropylene tubes. The samples will be stored in a freezer at −75±15° C. prior to analysis. Concentrations of compounds in the plasma samples will be analyzed using a LC-MS/MS method. WinNonlin (Phoenix™, version 6.1) or other similar software will be used for pharmacokinetic calculations. The following pharmacokinetic parameters will be calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data will be described using descriptive statistics such as mean, standard deviation. Additional pharmacokinetic or statistical analysis may be performed at the discretion of the contributing scientist, and will be documented in the data summary.

Biological Example 4: Mice CNS PK Study

The pharmacokinetics of compounds were evaluated in CD-1 mouse via Intravenous and Oral Administration. The iv dose was administered as a slow bolus in the Jugular vein, and oral doses were administered by gavage. The formulation for IV dosing is 5% DMSO in "20% HPBCD in water, and the PO formulation is 2.5% DMSO, 10% EtOH, 20% Cremphor EL, 67.5% D5W. The PK time point for the IV arm is 5, 15, 30 min, 1, 2, 4, 6, 8, 12, 24 hours post dose, and for PO arm is 15, 30 min, 1, 2, 4, 6, 8, 12, 24 hours post dose.

Plasma Samples Processing and Storage: Approximately 0.2 mL blood will be collected at each time point. Keep blood at room temperature and collect plasma within 15 min by centrifugation at 4000 g for 5 minutes in a 4° C.

centrifuge. Plasma samples will be stored in polypropylene tubes. The plasma samples will be stored in a freezer at −75±15° C. prior to analysis.

Brain Samples Processing and Storage: The mice will be fully exsanguinated prior to tissue collection. Procedure: open chest cavity, cut ventricle and perform a gentle iv saline flush (saline flush volume ~10 ml) with the animal placed head down at a 45 degree angle to facilitate blood removal. Tissue samples will be collected at adopted time point, quick frozen in ice box and kept at −75±15° C. All tissue samples will be weighted and homogenized with water by tissue weight (g) to water volume (mL) at ratio 1:3 before analysis. The actual concentration is the detected value multiplied by the dilution factor.

Concentrations of compounds in the plasma samples will be analyzed using a LC-MS/MS method. WinNonlin (Phoenix™, version 6.1) or other similar software will be used for pharmacokinetic calculations. The following pharmacokinetic parameters will be calculated, whenever possible from the plasma concentration versus time data: IV administration: $C_0$, CL, $V_d$, $T_{1/2}$, $AUC_{inf}$, $AUC_{last}$, MRT, Number of Points for Regression; PO administration: $C_{max}$, $T_{max}$, $T_{1/2}$, $AUC_{inf}$, $AUC_{last}$, F %, Number of Points for Regression. The pharmacokinetic data will be described using descriptive statistics such as mean, standard deviation. Additional pharmacokinetic or statistical analysis may be performed at the discretion of the contributing scientist, and will be documented in the data summary.

The following table lists the mice CNS PK parameters for certain compounds of the invention, which shows dramatically higher CNS penetration than AZD1775.

| Compound | Plasma $AUC_{last}$ (h*ng/mL) | Brain $AUC_{last}$ (h*ng/mL) | Brain/Blood Ratio |
| --- | --- | --- | --- |
| AZD1775 | 8,996 | 524 | 5.8% |
| Example 11 | 7,506 | 12,002 | 160% |
| Example 13 | 8,655 | 11,907 | 138% |
| Example 15 | 4,713 | 4,910 | 100% |

Biological Example 5: In Vivo Xenograft Studies

The CB.17 SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 mm³, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant. As shown below, 7 dose of Example 3 at 100 mg/kg leads to the complete regression of the tumor at day 18.

What is claimed is:

1. A compound of Formula (I):

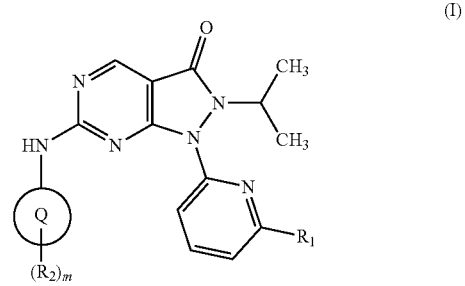

or a pharmaceutically acceptable salt, stereoisomer, or tautomer thereof, wherein:

Q is phenyl;

$R_1$ is $CF_2CH_3$, $C(CH_3)_2CF_3$, cyclopropyl, or cyclobutyl;

each $R_2$ is independently halo, alkyl, or heterocycloalkyl, wherein each heterocycloalkyl is optionally and independently substituted with one or more independently selected $R_d$ substituents;

each $R_d$ is independently halo, CN, $NO_2$, alkyl, alkenyl, alkynyl, C(O)alkyl, $C(O)NH_2$, C(O)NHOH, C(O)OH, C(O)O(alkyl), $NH_2$, NH(alkyl), NH(haloalkyl), NHC(O)alkyl, =NH, N[S(O)alkyl]alkyl, OH, O(alkyl), =O, $P(O)(alkyl)_2$, S(O)(NH)alkyl, cycloalkyl, cycloalkenyl, heterocycloalkyl, heterocycloalkenyl, aryl, or heteroaryl, wherein each alkyl is optionally and independently substituted with one or more independently selected $R_e$ substituents, and further wherein each cycloalkyl, cycloalkenyl, heterocycloalkyl, and heterocycloalkenyl is optionally and independently substituted with one or more independently selected $R_{e'}$ substituents, and each aryl and heteroaryl is optionally and independently substituted with one or more independently selected $R_{e''}$ substituents;

each $R_e$ is independently halo, CN, $NO_2$, C(O)alkyl, C(O)NHOH, C(O)O(alkyl), $NH_2$, NH(alkyl), NH(haloalkyl), NHC(O)alkyl, OH, O(alkyl), cycloalkyl, cycloalkenyl, heterocycloalkyl, heterocycloalkenyl, aryl, or heteroaryl;

each $R_{e'}$ is independently halo, CN, $NO_2$, alkyl, haloalkyl, alkylene-$NH_2$, alkylene-OH, alkylene-O(alkyl), alkenyl, alkynyl, C(O)alkyl, C(O)NHOH, C(O)O(alkyl), $NH_2$, NH(alkyl), NH(haloalkyl), NHC(O)alkyl, OH, O(alkyl), =O, cycloalkyl, cycloalkenyl, heterocycloalkyl, heterocycloalkenyl, aryl, or heteroaryl;

each $R_{e''}$ is independently halo, CN, $NO_2$, alkyl, haloalkyl, alkylene-$NH_2$, alkylene-OH, alkylene-O(alkyl), alkenyl, alkynyl, C(O)alkyl, C(O)NHOH, C(O)O(alkyl), $NH_2$, NH(alkyl), NH(haloalkyl), NHC(O)alkyl, OH, O(alkyl), cycloalkyl, cycloalkenyl, heterocycloalkyl, heterocycloalkenyl, aryl, or heteroaryl; and m is 1 or 2.

2. The compound according to claim 1, wherein the compound is represented by Formula (II):

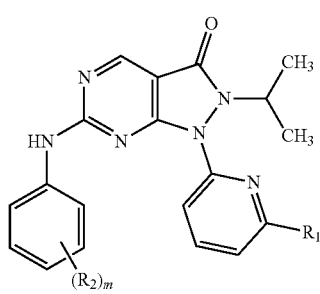
(II)

or a pharmaceutically acceptable salt, stereoisomer, or tautomer thereof,
wherein:
  m is 1.

3. The compound according to claim 2, or a pharmaceutically acceptable salt, stereoisomer, or tautomer thereof, wherein:
  $R_2$ is $C_{1-4}$ alkyl, $C_{1-4}$ haloalkyl, or 4- to 7-membered heterocycloalkyl, wherein the 4- to 7-membered heterocycloalkyl is optionally substituted with one or more independently selected $R_d$ substituents; and
  each $R_d$ is independently halo, CN, $NO_2$, $C_{1-4}$ alkyl, $C(O)C_{1-4}$ alkyl, $C(O)NH_2$, $C(O)OH$, $C(O)OC_{1-4}$ alkyl, $NH_2$, OH, $OC_{1-4}$ alkyl, or $C_{3-6}$ cycloalkyl.

4. The compound according to claim 3, or a pharmaceutically acceptable salt, stereoisomer, or tautomer thereof, wherein $R_1$ is $CF_2CH_3$, $C(CH_3)_2CF_3$, or cyclopropyl.

5. The compound according to claim 1, wherein the compound is represented by Formula (III):

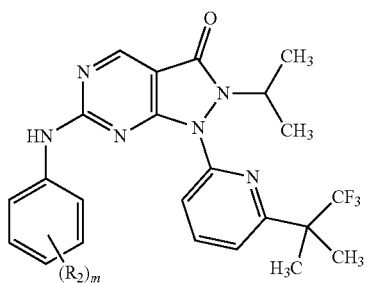
(III)

or a pharmaceutically acceptable salt, stereoisomer, or tautomer thereof.

6. The compound according to claim 1, or a pharmaceutically acceptable salt, stereoisomer, or tautomer thereof, wherein:
  each $R_2$ is independently F, $C_{1-4}$ alkyl, pyrrolidinyl, piperazinyl, or morpholinyl, wherein the piperazinyl is optionally substituted with one or more independently selected $R_d$ substituents;
  each $R_d$ is independently $C_{1-4}$ alkyl or $C_{3-6}$ cycloalkyl, wherein each $C_{1-4}$ alkyl is optionally and independently substituted with one or more independently selected $R_e$ substituents;
  each $R_e$ is an independently selected halo substituent; and
  m is 1.

7. The compound according to claim 1, wherein the compound is selected from the group consisting of:

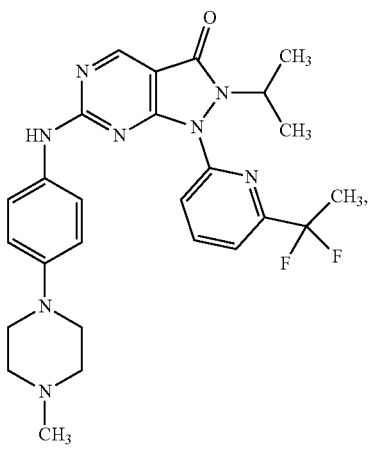

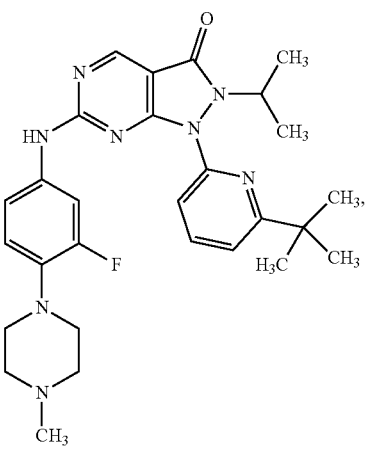

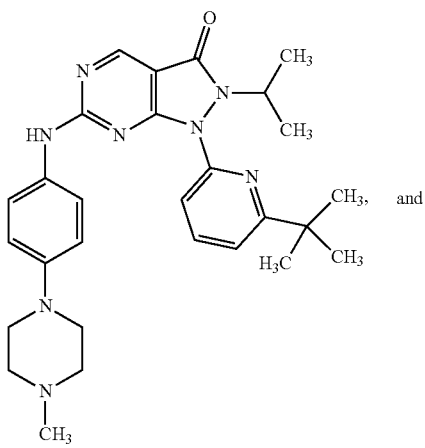
and

-continued
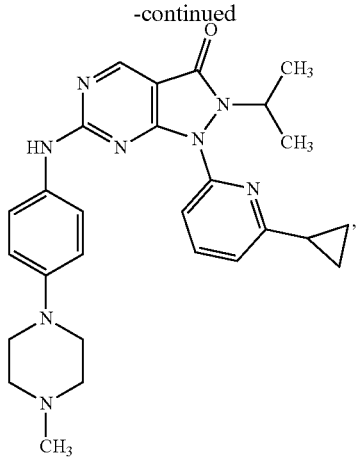
or a pharmaceutically acceptable salt or tautomer thereof.
8. A pharmaceutical composition comprising a pharmaceutically acceptable diluent or carrier and a compound according to claim 1, or a pharmaceutically acceptable salt, stereoisomer, or tautomer thereof.
9. A compound:
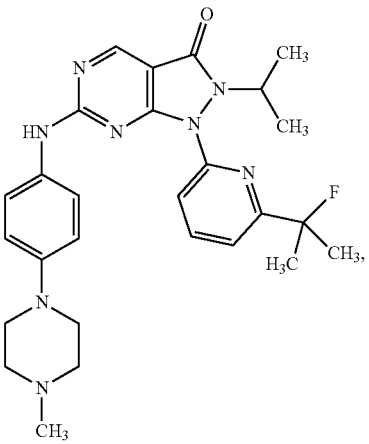 [SMILES: CC(C)n1c(=O)c2cnc(Nc3ccc(N4CCN(C)CC4)cc3)nc2n1-c1cccc(C(C)(C)F)n1]
or a pharmaceutically acceptable salt or tautomer thereof.
* * * * *